United States Patent
Holliday et al.

(10) Patent No.: US 10,299,960 B2
(45) Date of Patent: May 28, 2019

(54) CUSTOMIZED LASER EPITHELIAL ABLATION SYSTEMS AND METHODS

(71) Applicant: AMO Development, LLC, Santa Ana, CA (US)

(72) Inventors: Keith Holliday, Lake Forest, CA (US); Mark E. Arnoldussen, San Carlos, CA (US)

(73) Assignee: AMO DEVELOPMENT, LLC, Santa Ana, CA (US)

( * ) Notice: Subject to any disclaimer, the term of this patent is extended or adjusted under 35 U.S.C. 154(b) by 182 days.

(21) Appl. No.: 15/195,391

(22) Filed: Jun. 28, 2016

(65) Prior Publication Data

US 2016/0302968 A1    Oct. 20, 2016

Related U.S. Application Data

(60) Continuation of application No. 15/048,353, filed on Feb. 19, 2016, which is a division of application No.
(Continued)

(51) Int. Cl.
*A61F 9/008* (2006.01)
*G01N 1/10* (2006.01)
*G01N 33/04* (2006.01)

(52) U.S. Cl.
CPC ............ *A61F 9/00806* (2013.01); *G01N 1/10* (2013.01); *G01N 33/04* (2013.01);
(Continued)

(58) Field of Classification Search
CPC ............................ A61F 9/008–9/00819; A61F 9/00825–9/00829; A61F 9/00838;
(Continued)

(56) References Cited

U.S. PATENT DOCUMENTS

| 4,523,821 A | 6/1985 | Lang et al. |
| 4,665,913 A | 5/1987 | L'Esperance, Jr. |

(Continued)

FOREIGN PATENT DOCUMENTS

| DE | 19950791 A1 | 5/2001 |
| EP | 1639973 A2 | 3/2006 |

(Continued)

OTHER PUBLICATIONS

Borsutzky A., et al., "Tunable UV Radiation at Short Wavelengths (188-240 nm) Generated by Sum Frequency Mixing in Lithium Borate," Applied Physics B, 1991, vol. 52, pp. 380-384.
(Continued)

*Primary Examiner* — David Shay
(74) *Attorney, Agent, or Firm* — Johnson & Johnson Surgical Vision, Inc.

(57) ABSTRACT

Systems and methods to treat a region of a cornea of an eye having an epithelial layer disposed over a stromal layer. The system comprises a device to map a thickness of the epithelial layer over the region of the cornea to generate a map of epithelial thickness over the region, and a laser to generate a laser beam of an ablative radiation. A movable scan component is coupled to the laser to scan the laser beam over the region. A processor system is coupled to the laser and the movable scan component, and the processor system is configured to arrange pulses of laser beam to ablate the epithelial layer of the region in response to the map of epithelial thickness.

10 Claims, 21 Drawing Sheets

Related U.S. Application Data

12/122,319, filed on May 16, 2008, now Pat. No. 9,295,584.

(60) Provisional application No. 60/938,684, filed on May 17, 2007.

(52) U.S. Cl.
CPC ... *A61F 9/00817* (2013.01); *A61F 2009/0088* (2013.01); *A61F 2009/00846* (2013.01); *A61F 2009/00848* (2013.01); *A61F 2009/00872* (2013.01); *A61F 2009/00882* (2013.01); *H05K 999/99* (2013.01)

(58) Field of Classification Search
CPC .. A61F 2009/00844; A61F 2009/00848; A61F 2009/00851; A61F 2009/00872; A61F 2009/0088; A61F 2009/00882
USPC .............................................. 606/4–6, 10–13
See application file for complete search history.

(56) References Cited

U.S. PATENT DOCUMENTS

| | | | |
|---|---|---|---|
| 4,692,003 A | 9/1987 | Adachi et al. | |
| 4,718,418 A | 1/1988 | L'Esperance, Jr. | |
| 4,761,071 A | 8/1988 | Baron | |
| 4,863,260 A | 9/1989 | Gersten et al. | |
| 4,995,716 A | 2/1991 | Warnicki et al. | |
| 5,062,702 A | 11/1991 | Bille | |
| 5,144,630 A | 9/1992 | Lin | |
| 5,159,361 A | 10/1992 | Cambier et al. | |
| 5,258,791 A | 11/1993 | Penney et al. | |
| 5,293,871 A | 3/1994 | Reinstein et al. | |
| 5,329,322 A | 7/1994 | Yancey | |
| 5,359,373 A | 10/1994 | Koester et al. | |
| 5,423,801 A | 6/1995 | Marshall et al. | |
| 5,480,396 A | 1/1996 | Simon et al. | |
| 5,491,524 A | 2/1996 | Hellmuth et al. | |
| 5,505,724 A | 4/1996 | Steinert | |
| 5,512,965 A | 4/1996 | Snook | |
| 5,634,920 A | 6/1997 | Hohla | |
| 5,646,791 A | 7/1997 | Glockler | |
| 5,683,379 A | 11/1997 | Hohla | |
| 5,713,892 A | 2/1998 | Shimmick | |
| 5,742,626 A | 4/1998 | Mead et al. | |
| 5,784,162 A | 7/1998 | Cabib et al. | |
| 5,841,511 A | 11/1998 | D'Souza et al. | |
| 5,912,775 A | 6/1999 | Glockler | |
| 6,000,800 A | 12/1999 | Webb et al. | |
| 6,019,755 A | 2/2000 | Steinert | |
| 6,118,580 A | 9/2000 | Webb | |
| 6,155,684 A | 12/2000 | Bille et al. | |
| 6,203,539 B1 | 3/2001 | Shimmick et al. | |
| 6,245,059 B1 | 6/2001 | Clapham | |
| 6,264,328 B1 | 7/2001 | Williams et al. | |
| 6,271,914 B1 | 8/2001 | Frey et al. | |
| 6,271,915 B1 | 8/2001 | Frey et al. | |
| 6,286,958 B1 | 9/2001 | Koest et al. | |
| 6,293,939 B1 | 9/2001 | Steinert | |
| 6,299,311 B1 | 10/2001 | Williams et al. | |
| 6,315,727 B1 | 11/2001 | Coleman et al. | |
| 6,322,216 B1 | 11/2001 | Yee et al. | |
| 6,331,177 B1 | 12/2001 | Munnerlyn et al. | |
| 6,347,549 B1 | 2/2002 | Ryan et al. | |
| 6,409,345 B1 | 6/2002 | Molebny et al. | |
| 6,454,761 B1 | 9/2002 | Freedman | |
| 6,558,373 B1 | 5/2003 | Cowperthwaite | |
| 6,588,903 B2 | 7/2003 | Rathjen | |
| 6,592,574 B1 | 7/2003 | Shimmick et al. | |
| 6,613,041 B1 | 9/2003 | Schruender | |
| 6,635,051 B1 | 10/2003 | Hohla | |
| 6,663,619 B2* | 12/2003 | Odrich ................ A61F 9/008 606/10 |
| 6,666,857 B2 | 12/2003 | Smith | |
| 6,741,359 B2 | 5/2004 | Wei et al. | |
| 6,755,819 B1 | 6/2004 | Waelti | |
| 6,816,316 B2 | 11/2004 | Caudle et al. | |
| 6,922,250 B2 | 7/2005 | Fercher | |
| 6,932,475 B2 | 8/2005 | Molebny et al. | |
| 6,939,342 B2* | 9/2005 | Markman ........... A61F 9/00806 606/10 |
| 6,949,071 B1 | 9/2005 | Saied et al. | |
| 6,984,227 B2 | 1/2006 | Munnerlyn et al. | |
| 7,001,020 B2 | 2/2006 | Yancey et al. | |
| 7,008,415 B2 | 3/2006 | Yee et al. | |
| 7,036,934 B1 | 5/2006 | Youssefi et al. | |
| 7,044,602 B2 | 5/2006 | Chernyak | |
| 7,048,690 B2 | 5/2006 | Coleman et al. | |
| 7,077,838 B2 | 7/2006 | Wong | |
| 7,083,609 B2 | 8/2006 | Chernyak | |
| 7,084,986 B2 | 8/2006 | Hellmuth et al. | |
| 7,168,807 B2 | 1/2007 | Chernyak et al. | |
| 7,175,278 B2 | 2/2007 | Chernyak et al. | |
| 7,206,132 B2 | 4/2007 | Somani et al. | |
| 2002/0082629 A1 | 6/2002 | Cox et al. | |
| 2003/0176855 A1 | 9/2003 | Gross et al. | |
| 2003/0208190 A1 | 11/2003 | Roberts et al. | |
| 2004/0147910 A1 | 7/2004 | Fujieda | |
| 2005/0102008 A1 | 5/2005 | Wong | |
| 2005/0107775 A1 | 5/2005 | Huang et al. | |
| 2007/0282313 A1* | 12/2007 | Huang ................ A61F 9/00831 606/5 |
| 2008/0287928 A1 | 11/2008 | Arnoldussen et al. | |

FOREIGN PATENT DOCUMENTS

| | | | | |
|---|---|---|---|---|
| WO | WO 94/07447 | * | 4/1994 | ......... A61F 9/00804 |
| WO | 9737622 A1 | | 10/1997 | |
| WO | 0108547 A2 | | 2/2001 | |
| WO | WO 01/28410 | * | 4/2001 | ......... A61F 9/00804 |
| WO | 0167978 A1 | | 9/2001 | |

OTHER PUBLICATIONS

International Search Report and Written Opinion for Application No. PCT/US2007/084341, dated Mar. 10, 2008, 13 pages.
International Search Report for Application No. PCT/US08/063978, dated Dec. 22, 2008, 5 pages.
U.S. Appl. No. 11/937,760, filed Nov. 9, 2007, first named inventor: Mark Arnoldussen.

* cited by examiner

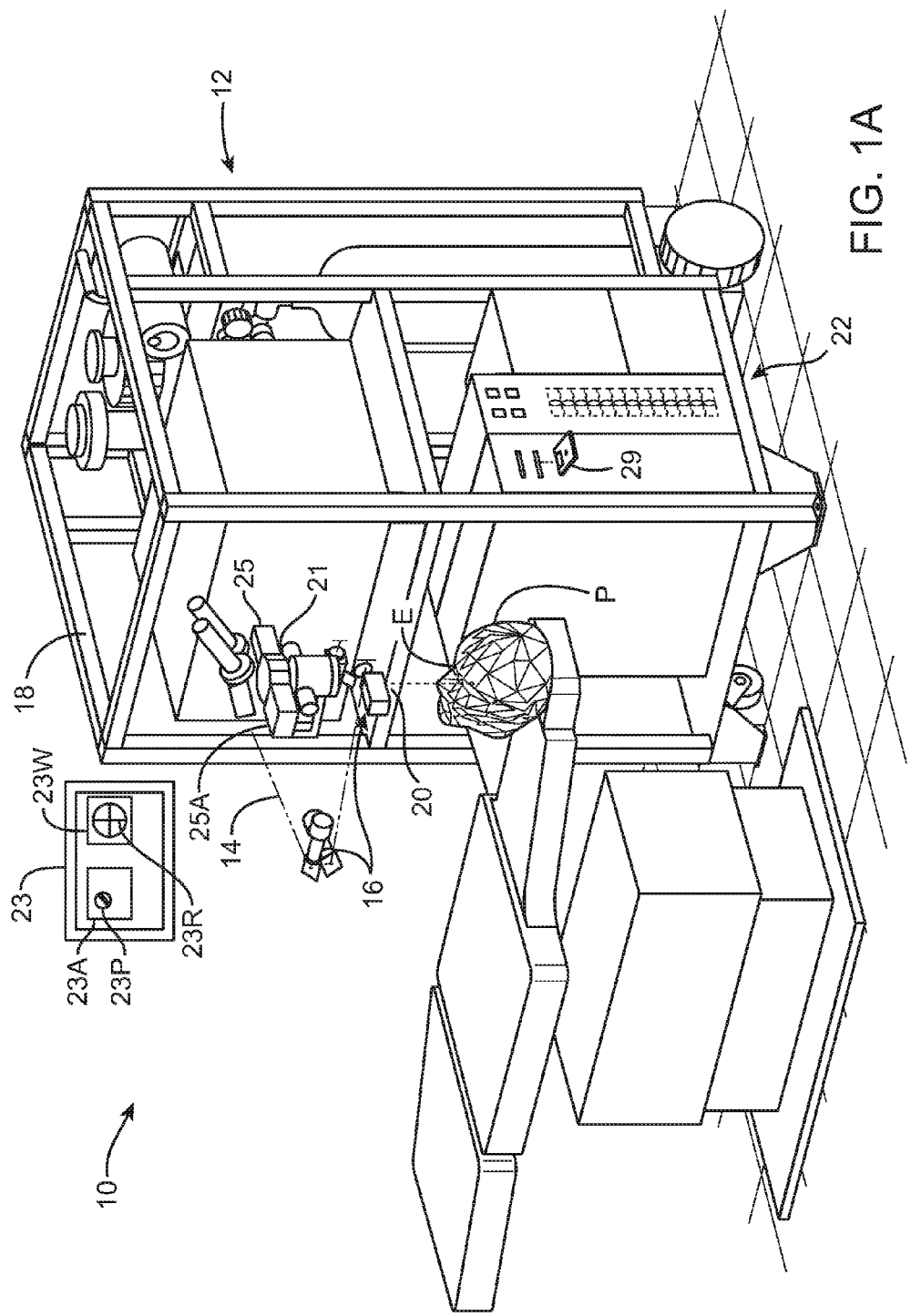

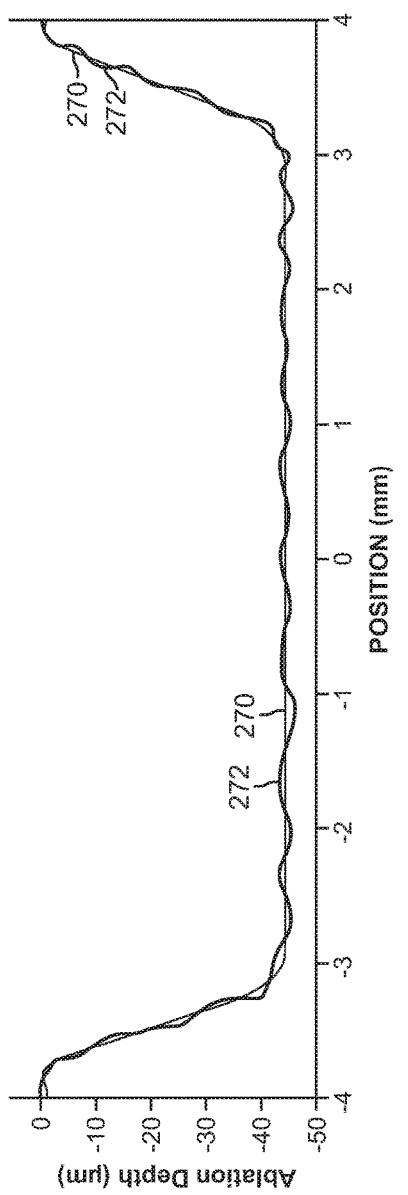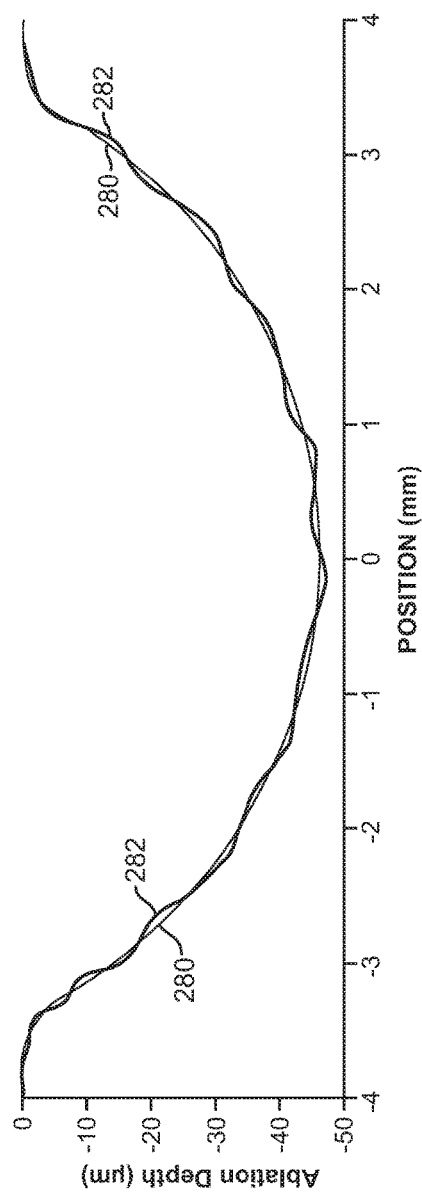

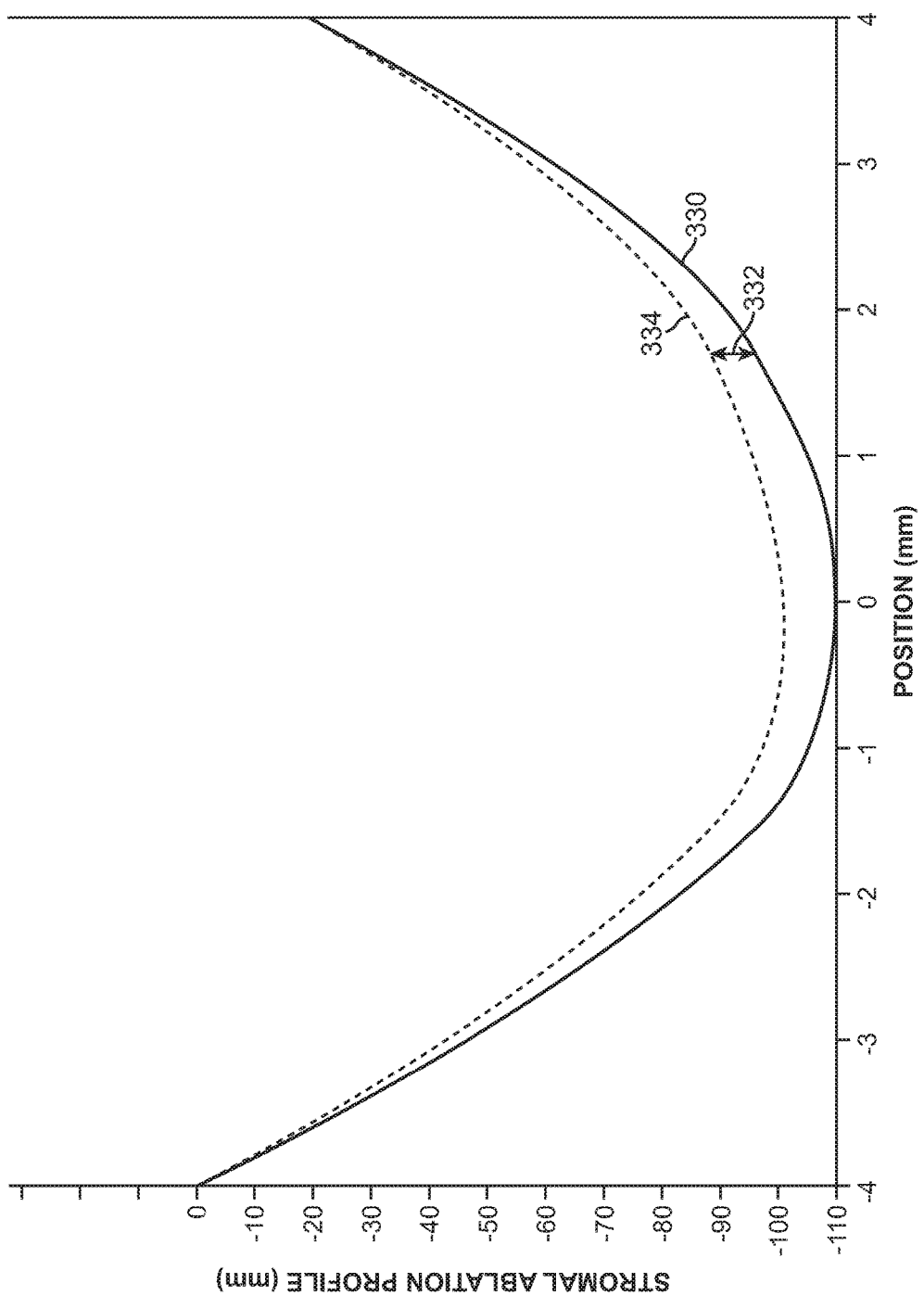

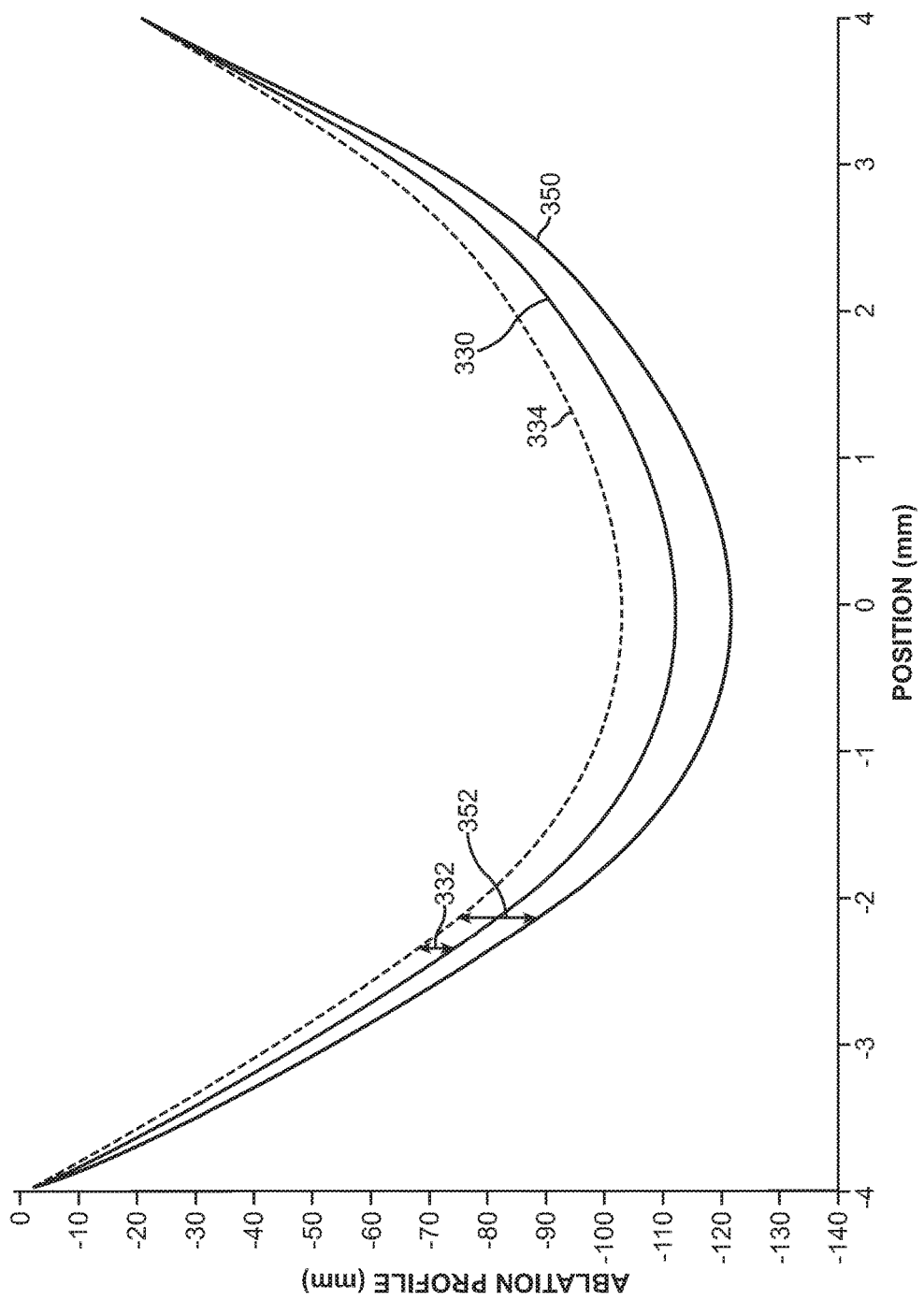

CUSTOMIZED LASER EPITHELIAL ABLATION SYSTEMS AND METHODS

CROSS-REFERENCES TO RELATED APPLICATIONS

The present application is a continuation of U.S. patent application Ser. No. 15/048,353, filed Feb. 19, 2016 and titled CUSTOMIZED LASER EPITHELIAL ABLATION SYSTEMS AND METHODS, which is a divisional of U.S. patent application Ser. No. 12/122,319, filed May 16, 2008 and titled CUSTOMIZED LASER EPITHELIAL ABLATION SYSTEMS AND METHODS, which claims the benefit under 35 USC 119(e) of U.S. Provisional Patent Application No. 60/938,684 filed May 17, 2007; the full disclosure of each of which is incorporated herein in its entirety by reference.

BACKGROUND OF THE INVENTION

The present invention relates generally to the contouring of optical surfaces. More specifically, the present invention relates to devices, systems, and methods for contouring optical surfaces with laser beams. Merely by way of example, devices systems and methods of the present invention are described with reference to the treatment of eyes during photorefractive keratectomy (PRK) and the like. The devices, systems and methods of the present invention can be used with other optical contouring applications, for example, the fabrication of spectacles and contact lenses.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, frequency multiplied solid-state lasers, and the like. The lasers of these laser systems typically deliver a series of laser beam pulses during a treatment.

Known corneal correction treatment methods have generally been successful in correcting standard vision errors, such as myopia, hyperopia, astigmatism, and the like. By customizing an ablation pattern based on wavefront measurements, it may be possible to correct minor aberrations so as to reliably and repeatedly provide visual acuity greater than 20/20. Such detailed corrections will benefit from an extremely accurate ablation of tissue.

With many laser ablation procedures, the epithelium is generally removed so that the permanent optical correction can be ablated into the stroma and/or Bowman's membrane. With PRK the epithelium is removed to expose Bowman's membrane and/or the stroma. Epithelial removal has been accomplished mechanically and with laser ablation of the epithelial layer. Mechanical removal of the epithelial layer can be accomplished with mechanical scraping of the epithelial tissue layer to expose Bowman's membrane and/or the stroma. Another mechanical approach is to remove the epithelium with a brush. With Laser-Assisted Sub-Epithelial Keratectomy (LASEK), the epithelial layer is removed from the cornea as a sheet so that the layer can be replaced following the ablation of stromal tissue. Although these mechanical methods of epithelial removal have been successful clinically, mechanical removal of the epithelium takes time and can be perceived by the patients as invasive because the surgeon will touch the front surface of the eye with surgical instruments. Even though topical anesthesia is often applied to the cornea so that the patient cannot feel the surgeon touching his or her cornea, the patient can become nervous while the surgeon touches the front surface of the eye with the instruments, possibly delaying the procedure.

Laser ablation of the epithelium, also referred to as trans-epithelial ablation, can be less invasive and faster than mechanical approaches to removal of the epithelium. However, work in connection with the present invention suggests that the known methodologies for laser ablation of the epithelium may be less than ideal, and in some instances the epithelial layer may not be ablated uniformly. Thus, a surgeon will often mechanically scrape the epithelium after laser removal of the epithelium to ensure that no residual epithelial debris remains before ablating stromal tissue.

In light of the above, it would be desirable to provide more accurate trans-epithelial ablations over large areas of the cornea, for example customized trans-epithelial ablations, while avoiding at least some of the limitations of known systems.

SUMMARY OF THE INVENTION

The present invention provides systems and methods for ablating tissue in response to characteristics of the cornea, for example the corneal epithelial layer. The characteristics of the cornea can be used so as to improve the accuracy of the ablation and/or correction of the eye.

In a first aspect, embodiments of the present invention provide a method for treating a region of a cornea of an eye. The region comprises an epithelial layer disposed over a stromal layer. A thickness of the epithelial layer is measured, for example mapped, in the region of the cornea. The region is irradiated with laser beam pulses to ablate the epithelial layer of the region in response to the epithelial thickness.

In some embodiments, an optical property of the eye is mapped, and the region is irradiated in response to the mapped optical property and the mapped epithelial thickness. The optical property of the eye can be mapped at locations distributed in two dimensions across the pupil of the eye, and the thickness of the epithelium can be mapped at locations distributed in two dimensions. The stromal layer can be ablated in response to the mapped epithelial layer thickness, and the map of epithelial thickness can be registered with an iris of the eye.

In some embodiments, an arrangement of laser beam pulses is determined using the mapped epithelial thickness and irradiation of the region is initiated using the determined arrangement. The epithelial layer can be ablated in response to the mapped epithelial thickness to expose at least one of the stromal layer or a Bowman's membrane. Delivery of the epithelial arrangement of pulses can be interrupted in response to a tissue fluorescence of at least one of the epithelial layer, a Bowman's membrane or the stromal layer.

In some embodiments, an optical property of the eye is determined and the region irradiated in response to the determined optical property of the eye and the mapped thickness of the epithelial layer. A first arrangement of laser beam pulses can be determined in response to the map of the epithelial layer and a second arrangement of laser beam pulses determined in response to the optical property of the eye. The first arrangement and the second arrangement may comprise locations of the laser beam pulses.

In some embodiments, the first arrangement of laser beam pulses may remove the epithelial layer to expose at least one of the stromal layer or a Bowman's membrane and the second arrangement of laser beam pulses may ablate a portion of the stromal layer to correct the optical property. Alternatively or in combination, the first arrangement of laser beam pulses may be combined with the second arrangement of laser beam pulses such that a portion of the second arrangement of laser beam pulses irradiates the epithelial layer and a portion of the first arrangement of laser beam pulses irradiates the stroma. In specific embodiments, the portion of the second arrangement that irradiates the epithelium may be interspersed among pulses of the first arrangement, and the portion of the first arrangement that irradiates the stroma may be interspersed among pulses of the second arrangement.

In some embodiments, energy is transmitted through the epithelial layer and/or reflected from an interface between the epithelial layer and the stromal layer while the region is mapped, and the energy reflected from the interface may comprise at least one of optical energy or ultrasound energy.

In another aspect, embodiments of the present invention provide a system to treat a region of a cornea of an eye, in which the region comprises an epithelial layer disposed over a stromal layer. The system comprises a device to measure a thickness of the epithelial layer, and a laser to generate a laser beam of an ablative radiation. A movable scan component is coupled to the laser to scan the laser beam over the region. A processor system is coupled to the laser and the movable scan component. The processor system comprises a tangible medium configured to arrange pulses of laser beam to ablate the epithelial layer of the region in response to the epithelial thickness.

In many embodiments the device to measure the thickness of the epithelial layer comprises at least one of an ultrasound array, an optical coherence tomography machine, a confocal microscope or a Scheimpflug imaging system In another aspect, embodiments of the invention provide a system to treat a region of a cornea of an eye. The region comprises an epithelial layer disposed over a stromal layer. The system comprises a device to map a thickness of the epithelial layer over the region of the cornea to generate a map of epithelial thickness over the region, and a laser to generate a laser beam of an ablative radiation. A movable scan component is coupled to the laser to scan the laser beam over the region. A processor system is coupled to the laser and the movable scan component. The processor system comprises a tangible medium configured to arrange pulses of laser beam to ablate the epithelial layer of the region in response to the map of epithelial thickness.

In some embodiments, the processor system is configured to ablate the epithelial layer in response to the epithelial layer map thickness to expose at least one of the stromal layer or a Bowman's membrane. The processor system can be configured control the laser and/or moveable scan component to ablate the stromal layer in response to the map of thickness of the epithelial layer. The processor system can be configured to determine a refractive optical property of the eye and irradiate the region in response to the determined optical property and the map of the thickness of the epithelial layer.

In specific embodiments, the refractive optical property device may comprise at least one of a trial lens, a phoropter, an auto-refractor, a spatially resolved refractometer, a corneal topographer, or a Hartmann-Shack wavefront sensor. The device to map the epithelial layer may comprise at least one of an ultrasound array, an optical coherence tomography machine, a confocal microscope or a Scheimpflug imaging system.

The processor system may be configured to register the map of epithelial thickness with an iris of the eye and adjust the arrangement of pulses in response to an orientation of the eye.

In some embodiments, the system includes an imaging system to form an image of a tissue auto-fluorescence of the cornea that is visible to a user, wherein the processor system is configured to interrupt delivery of the epithelial arrangement of pulses in response to user input while the user views the tissue auto-fluorescence.

In another aspect, embodiments of the present invention provide a method for treating a region of a cornea of an eye. The eye comprises an epithelial layer over a stromal layer. An epithelial basis profile is determined for the epithelial layer and a stromal basis profile for the stromal layer. The stromal basis profile is different from the epithelial basis profile. An epithelial arrangement of laser beam pulses can be determined that corresponds to ablation of the epithelial layer of the region to a target epithelial ablation profile. The region is irradiated with the epithelial arrangement.

In some embodiments, the epithelial arrangement can be determined in response to the epithelial basis profile and the target ablation profile. The epithelial basis profile may correspond to tissue removed with an epithelial laser beam pulse to the epithelial layer, and the stromal basis profile may correspond to tissue removed with a stromal laser beam pulse to the stromal layer. In specific embodiments, the epithelial arrangement may be determined with a plurality of epithelial basis profiles that correspond to epithelial tissue ablated with a plurality of sizes of the laser beam.

In some embodiments, an arrangement of laser beam pulses for ablation of Bowman's membrane may be determined.

In specific embodiments, a thickness of the epithelial layer of the region can be mapped to generate a map of epithelial thickness over the region, and the epithelial arrangement determined in response to the map of epithelial thickness over the region.

In some embodiments, a stromal arrangement of laser beam pulses corresponds to ablation of a stromal layer of the region to a target stromal ablation profile. The stromal arrangement can be determined with a stromal basis profile that corresponds to stromal tissue removed with laser beam pulses to the stromal layer. The region can be irradiated with the stromal arrangement of laser beam pulses to contour the region. The stromal arrangement may be determined in response to the stromal basis profile and the target stromal ablation profile. The stromal arrangement can be determined with a plurality of stromal basis profiles that correspond to stromal tissue ablated with a plurality of sizes of the laser beam. An optical property of the eye over the region can be mapped to generate an optical property profile over the region, and the stromal arrangement is determined in response to the optical property profile. The epithelial arrangement of pulses can be delivered to the epithelial layer and the stromal arrangement of pulses is delivered to the stromal layer.

In some embodiments, the epithelial arrangement of pulses can be combined with the stromal arrangement of pulses, and several pulses of the epithelial arrangement are delivered to the stromal layer and several pulses of the epithelial arrangement are delivered to the epithelial layer. In specific embodiments, the several pulses of the epithelial arrangement that are delivered to the stromal layer may be interspersed among several pulses of the stromal arrangement that are delivered to the stromal layer. The several pulses of the stromal arrangement that are delivered to the epithelial layer may be interspersed among several pulses of the epithelial arrangement that are delivered to the epithelial layer In some embodiments of the present invention, a method is provided for treating a region of a cornea of an eye with an epithelial layer over a stromal layer and an epithelial basis profile determined for the epithelial layer and a stromal basis profile determined for the stromal layer. An epithelial arrangement of laser beam pulses is determined that corresponds to ablation of the epithelial layer of the region to a target epithelial ablation profile. The stromal basis profile is different from the epithelial basis profile. The region is irradiated with the epithelial arrangement.

In some embodiments, a stromal arrangement of laser beam pulses is determined that corresponds to ablation of a stromal layer of the region to a target stromal ablation profile. The region can be irradiated with the stromal arrangement of laser beam pulses to contour the region. The epithelial arrangement of pulses may be combined with the stromal arrangement of pulses, and several pulses of the epithelial arrangement delivered to the stromal layer and several pulses of the epithelial arrangement delivered to the epithelial layer.

In another aspect, embodiments of the present invention provide a system to treat a region of a cornea of an eye. The eye comprises an epithelial layer over a stromal layer. The system includes a laser to generate a beam and the laser beam comprises pulses of an ablative radiation, and a movable scan component to scan the laser beam over the region of the cornea to ablate the region. The system may include a processor system coupled to the laser and the movable scan component to scan the laser beam over the region. The processor system comprises a tangible medium configured to store an epithelial basis profile for the epithelial layer and a stromal basis profile for the stromal layer, the epithelial basis profile is different from the stromal basis profile. The processor system can be configured to determine an epithelial arrangement of the laser beam pulses in response to a target epithelial ablation profile and the epithelial basis profile.

In some embodiments, a peripheral portion of the epithelial basis profile corresponds to concave surface curvature ablated with a pulse of the laser beam and an inner portion of the basis profile corresponds to convex surface curvature ablated with the laser beam pulse. The epithelial basis profile may correspond to tissue removed with an epithelial laser beam pulse to the epithelial layer, and the stromal basis profile corresponds to tissue removed with a stromal laser beam pulse to the stromal layer. The processor system can be configured to combine the epithelial arrangement of laser beam pulses with the epithelial basis profile to determine a calculated epithelial tissue ablation profile and compare the calculated profile with the target profile. In specific embodiments, the processor system comprises a plurality of epithelial basis profiles that correspond to sizes of the laser beam.

In some embodiments, the processor system is configured to determine a stromal arrangement of the laser beam pulses in response to a target stromal ablation profile and the stromal basis profile. The processor system can be configured to combine the stromal arrangement of laser beam pulses with the stromal basis profile to determine a calculated stromal tissue ablation profile and compare the calculated stromal ablation profile with the target stromal ablation profile. In specific embodiments, the processor system comprises a plurality of ablation basis profiles that correspond to sizes of the laser beam.

In some embodiments, the processor system is configured to determine at least one of the epithelial arrangement or the stromal arrangement in response to an optical property map of the region. The processor system can be configured to deliver the epithelial arrangement of pulses to the epithelial layer and the stromal arrangement of pulses to the stromal layer. In specific embodiments, the epithelial arrangement of pulses may be combined with the stromal arrangement of pulses, and several pulses of the epithelial arrangement are delivered to the stromal layer and several pulses of the stromal arrangement are delivered to the epithelial layer.

In some embodiments, the processor system is configured to store the epithelial arrangement of pulses and the stromal arrangement of pulses in a treatment table comprising a sequence of pulses. The treatment table sequence can comprise several smaller pulses before several larger pulses to expand the beam from the smaller pulses to the larger pulses several times during the treatment.

In some embodiments, the processor system comprises a tangible medium configured to store Bowman's basis profile for ablation of Bowman's layer, and the Bowman's basis profile may be different from the stromal basis profile and the epithelial basis profile. The processor system can be configured to determine a Bowman's arrangement of the laser beam pulses in response to the Bowman's basis profile.

In another aspect, embodiments of the present invention provide a method for treating a region of a cornea of an eye in which the eye comprises a Bowman's layer over a stromal layer. A Bowman's basis profile is provided for the Bowman's layer and a stromal basis profile is determined for the stromal layer. The stromal basis profile may be different from the Bowman's basis profile. A Bowman's arrangement of laser beam pulses is determined that corresponds to ablation of the Bowman's layer of the region to a target Bowman's ablation profile. The region is irradiated with the Bowman's arrangement.

In some embodiments, a stromal arrangement of laser beam pulses is determined that correspond to ablation of a stromal layer of the region to a target stromal ablation profile. The region may be irradiated with the stromal arrangement of laser beam pulses to contour the region. The stromal arrangement can be determined in response to the stromal basis profile and the target stromal ablation profile.

In a further aspect, embodiments of the present invention provide a system to treat a region of a cornea of an eye in which the eye comprises a Bowman's layer over a stromal layer. The system comprises a laser to generate a beam in which the beam comprises pulses of an ablative radiation.

The system also comprises a movable scan component to scan the laser beam over the region of the cornea to ablate the region. A processor system may be coupled to the laser and the movable scan component to scan the laser beam over the region. The processor system may comprise a tangible medium configured to store a Bowman's basis profile for the Bowman's layer and a stromal basis profile for the stromal layer. The Bowman's basis profile may be different from the stromal basis profile, and the processor system may be configured to determine a Bowman's arrangement of the laser beam pulses in response to a target Bowman's ablation profile and the Bowman's basis profile.

In some embodiments, the processor system may be configured to determine a stromal arrangement of the laser beam pulses in response to a target stromal ablation profile and the stromal basis profile. The processor system may be configured to combine the stromal arrangement of laser beam pulses with the stromal basis profile to determine a calculated stromal tissue ablation profile and compare the calculated stromal ablation profile with the target stromal ablation profile. The processor system may comprise a plurality of ablation basis profiles that correspond to sizes of the laser beam.

In another aspect, embodiments of the present invention provide a method for contouring a region of a cornea of an eye. The region comprises an epithelial layer disposed over a stromal layer. A thickness of an epithelial layer of the region is mapped. A refractive optical property of the region is determined, and a desired optical profile to correct the refractive optical property is determined. A healed profile of the epithelial layer over the stromal layer is determined in response to the desired optical profile and the mapped epithelial layer thickness. The stromal layer is ablated to a profile in response to the healed epithelial layer profile to contour the region and correct the optical property of the eye.

In some embodiments, the optical property comprises at least one of a manifest refraction, a cycloplegic refraction, an auto-refraction, a Zernike coefficient, a Fourier coefficient or a wavefront elevation map. An epithelial component of the optical property and a remainder component of the optical property can be determined. The epithelial component corresponds to the mapped thickness of the epithelial layer. The epithelial component may be subtracted from the optical property to determine the remainder component. The stromal layer profile can be ablated in response to the remainder component and the healed epithelial layer component.

In some embodiments, a healed profile of the stromal layer is determined, and the stromal layer ablation profile determined in response to the healed stromal layer profile and the healed epithelial layer profile.

In another aspect, embodiments of the present invention provide a system for contouring a region of a cornea of an eye. The region comprises the epithelial layer disposed over a stromal layer. The system comprises a laser to generate an ablative laser beam, and an epithelial thickness mapping device to map a thickness of an epithelial layer of the region. A processor system comprises a tangible medium configured to determine a desired optical profile to correct an optical property of the eye. The processor system is configured to determine a healed profile of the epithelial layer over the stromal layer in response to the desired optical profile and the mapped epithelial layer thickness. The processor system is coupled to the laser to ablate a profile in the stromal layer in response to the healed epithelial layer profile to contour the region and correct the optical property of the eye. In specific embodiments, the optical property comprises at least one of a manifest refraction, a cycloplegic refraction, an auto-refraction, or a wavefront elevation map.

In some embodiments, the processor system can be configured to determine an epithelial component of the optical property and a remainder component of the optical property, and the epithelial component corresponds to the mapped thickness of the epithelial layer. The processor system can be configured to subtract the epithelial component from the optical property to determine the remainder component. The processor system may be configured to ablate the stromal layer profile in response to the remainder component and the healed epithelial component.

In some embodiments, the processor system is configured to determine a healed profile of the stromal layer. The processor system may be configured to determine the stromal layer ablation profile in response to the healed stromal layer profile and the healed epithelial layer profile.

BRIEF DESCRIPTION OF THE DRAWINGS

FIG. 1A is a perspective view of a laser ablation system for incorporating embodiments of the present invention;

FIG. 5E is a schematic illustration of a target epithelial ablation profile and an estimated epithelial ablation profile determined by combining the epithelial basis data with an epithelial arrangement of laser beam pulses, according to embodiments of the present invention;

FIG. 5F is a schematic illustration of a target stromal ablation profile and an estimated stromal ablation profile determined by combining the stromal basis data with a stromal arrangement of laser beam pulses, according to embodiments of the present invention;

FIG. 6C is a schematic illustration of a stromal ablation profile map to correct refractive optical properties of the eye in response to the refractive optical properties profile map as in FIG. 6B, according to embodiments of the present invention;

FIG. 7B is a schematic illustration of a stromal ablation profile map in response to the map of estimated corneal epithelial thickness following ablation as in FIG. 7A, the profile map of corneal epithelial thickness as in FIG. 6A and the profile map of refractive optical properties of the eye as in FIG. 6B, according to embodiments of the present invention;

DETAILED DESCRIPTION OF THE INVENTION

Figure 1B:
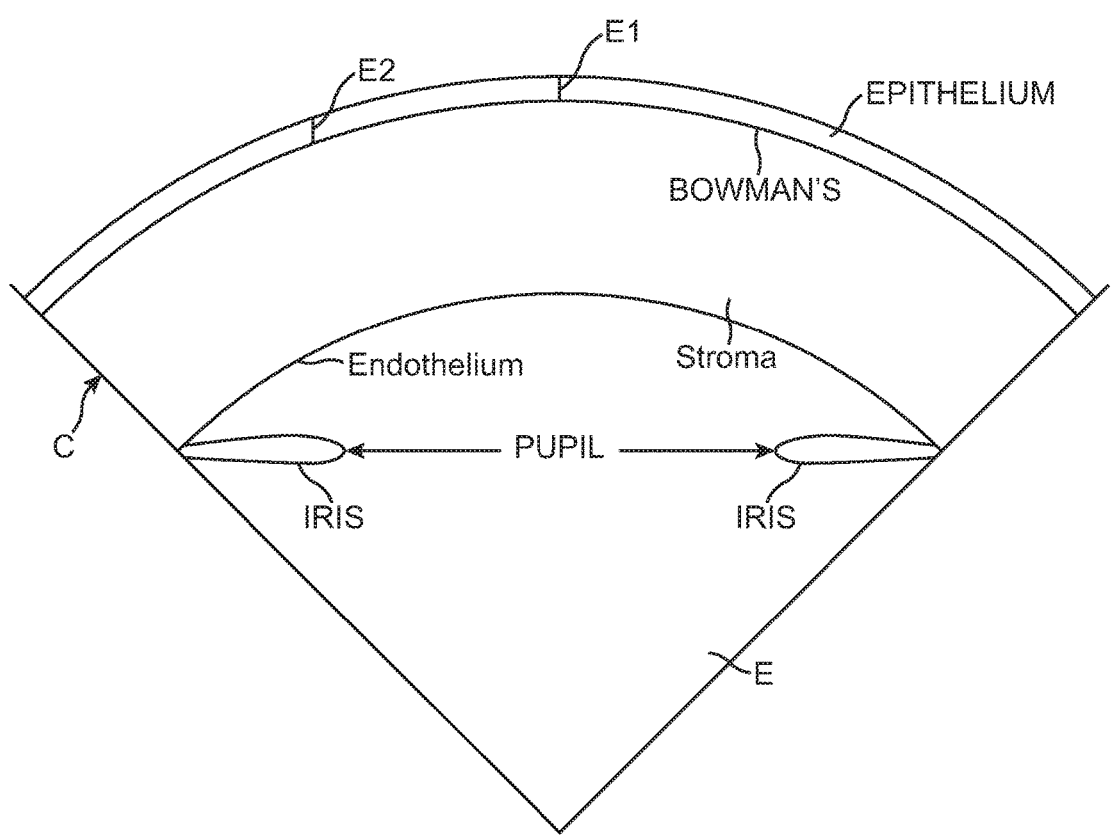
FIG. 1B illustrates profiles of mapped tissue structures of an eye, according to embodiments of the present invention.

The present invention is particularly useful for enhancing the accuracy and efficacy of laser eye surgical procedures, such as photorefractive keratectomy (PRK), phototherapeutic keratectomy (PTK), and the like. Preferably, the present invention can provide enhanced optical accuracy of refractive procedures and improved patient comfort during the procedure by improving removal of the corneal epithelium. Hence, while the system and methods of the present invention are described primarily in the context of a laser eye surgery system for treating a cornea of the eye, it should be understood the techniques of the present invention may be adapted for use in alternative ablation procedures.

The techniques of the present invention can be readily adapted for use with existing laser systems. By providing a more rapid (and hence, may be less prone to error) methodology for correcting optical errors of an eye, the present invention facilitates sculpting of the cornea so that treated eyes may regularly receive a desired optical correction having improved vision with minimal discomfort to a patient.

Referring now to FIG. 1A, a laser eye surgery system 10 for incorporating the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. An input device 20 is used to align laser system 10 with patient P. A microscope 21 is mounted on the delivery optics support structure. Microscope 21 comprises an imaging system to image a cornea of eye E. The laser eye surgery system 10 may include a display 23 that provides an image of eye E that is visible to the user. A video camera 25 can be optically coupled to microscope 21 to provide an image of the eye E on the display as seen through the microscope.

Microscope 21 transmits visible light, and the operator can view tissue auto-fluorescence of the epithelial layer while the laser ablates corneal tissue. The operator can interrupt the treatment in response to penetration of the epithelial layer, for example by lifting a foot switch pedal. Microscope 21 may comprise at least one lens to form an optical image of the tissue fluorescence that is visible to the operator such that the operator can detect penetration of the epithelial layer based on the optical feedback. In some embodiments, video camera 25 comprises a camera sensitive to visible light and at least a portion of the epithelial fluorescence comprises visible light, such that epithelial fluorescence can be seen with video camera 25. In some embodiments, a second video camera 25A can be coupled to microscope 21. Second camera 25A comprises a sensor sensitive to UV light to detect epithelial fluorescence. Second camera 25A can be triggered off the laser fire signal, such that each pulse of the treatment can be shown on the display, for example fluorescence from individual pulse 23P. Second video camera 25A may comprise an electronic shutter synchronized to the laser trigger such that the shutter is open for no more than about 1 ms, for example no more than 100 us, or even no more than 50 us, when the laser fires to enhance visibility of the epithelial fluorescence. Although a microscope is shown, in some embodiments a camera lens can be used to image the tissue fluorescence, such that the image of the tissue fluorescence can be shown on the display.

In some embodiments, the laser pulses may be sorted such that the user can see penetration of the epithelial layer, as described in U.S. Pat. App. No. 60/865,342, filed Nov. 10, 2006, entitled, "Operator-Controlled Scanning Laser Procedure Designed for Large-Area Epithelium Removal," the full disclosure of which is incorporated herein by reference.

In some embodiments the laser may automatically detect penetration of the epithelial layer as described in U.S. Pat. Nos. 5,505,724; 6,019,755; and U.S. Pat. No. 6,293,939 entitled "Epithelium Removal".

In many embodiments, a sudden reduction in fluorescence, for example either an average amount or a number of pixels of an image of fluorescence, can be measured and used to find and/or determine breakthrough, for example penetration, of the epithelial layer, for example when the measured fluorescence decreases from a first value above a threshold fluorescence amount to a second value below the threshold fluorescence amount so as to indicate penetration and/or breakthrough of the epithelial layer. In response to the detected penetration and/or breakthrough, the treatment algorithm and/or treatment program may stop ablation for safety and/or change treatment modes, for example to selectively ablate epithelium and/or to perform a refractive ablation of the stroma. Systems and methods of detecting at least one of penetration, breakthrough or clearance of the epithelial layer and automated removal of the epithelium in response to epithelial fluorescence are described in U.S. patent Ser. No. 12/121,635, the full disclosure of which is incorporated herein by reference. In various embodiments, the laser eye surgery system 10 includes at least some portions of a Star S3 Active Trak™ Excimer Laser System and/or a STAR S4 IR™ Excimer Laser System with Variable Spot Scanning (VSS™) and WaveScan WaveFront® System available from VISX, INCORPORATED of Santa Clara, Calif., the LADAR Vision® system commercially available from Alcon of Fort Worth; TX, the Zyoptix® Systems commercially available from Bausch & Lomb of Rochester N.Y.; the EC-5000 Series of excimer laser systems commercially available from NIDEK of Gamagori, Japan, the OPD Scan II also available from NIDEK; the MEL 80™ Excimer Laser and WASCA™ analyzer, both commercially available from Carl Zeiss Meditec, Inc. of Dublin, Calif., and the Wavescan Allegretto laser system with Tscherning aberrometer.

Laser eye surgery system 10 may comprise an eye tracker 19. Eye tracker 19 may comprise, for example, an eye tracker as commercially available in the Star S3 Active Trak™ Excimer laser system and/or the STAR S4 IR™ Excimer Laser System with Variable Spot Scanning (VSS™). Eye tracker 19 may comprise optical components microscope 21. The eye tracking system may comprise at least some optical components separate from the microscope, for example as described in U.S. Pat. No. 6,322,216. Eye tracker 19 can be in communication with the embedded computer so as to offset the position of the laser beam pulse in response to a measured position of the eye. The processor may comprise a processor system with at least one processor, for example a plurality of processors, such as a processor for tracking the eye, a processor to control the laser and at least one processor to control positions of scanning elements, sensors and laser firing. The processor system may comprise a distributed processor system with a first processor to calculate a treatment table, for example at a research facility, and a second processor, for example of the laser system, to ablate the eye with the treatment table from the first processor.

The display 23 may comprise windows to show images of the eye, for example a first window 23W and a second window 23A. First window 23A can be coupled to video camera 25 to show the image of the eye E as seen through the operating microscope. First window 23W may show structures visible to the operator, for example a reticule 23R, and the image of the eye including the iris and pupil. Video camera 23 may comprise a color video camera to show a color image of the eye to the operator on the display. Second window 23A can be coupled to second video camera 25A. The second video camera 25A can be coupled to a frame grabber of the embedded processor to grab an image for each pulse of the laser treatment and display the image from each pulse in window 23A of the display, so as to minimized dropped frames and facilitate detection of penetration through the epithelium. The camera synchronized to the laser beam pulse can improve epithelial fluorescence imaging and may be used for detection of penetration where the display is shown to an operator and/or where the laser pulse firing is stopped automatically. Although reference is made to a video camera, the fluorescence sensor can comprise many known sensors sensitive to fluorescence such as at least one of an area sensor, a line sensor, a CCD array, a gated image intensifier, photomultiplier tube, a photodiode, a phototransistor or a cascade detector.

While the input device 20 is here schematically illustrated as a joystick, it should be understood that a variety of input mechanisms may be used. Suitable input mechanisms may include trackballs, touch screens, foot-pedals or a wide variety of alternative pointing devices. Still further alternative input mechanisms include keypads, data transmission mechanisms such as an Ethernet, intranet, internet, a modem, or the like.

Laser 12 generally comprises an excimer laser, ideally comprising an argon-fluorine laser producing pulses of laser light having a wavelength of approximately 193 nm. The pulse of laser light typically has a fixed pulse duration having a full width half maximum (FWHM) of about 15 nanoseconds during a treatment. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193-215 nm) such as those disclosed in U.S. Pat. Nos. 5,144,630 and 5,742,626; Borsurtky et al., "Tunable UV Radiation at Short Wavelengths (188-240 nm) Generated by Sum Frequency Mixing in Lithium Borate," Appl. Phys. 61:529-532 (1995), and the like. The laser energy may comprise a beam formed as a series of discreet laser pulses. A variety of alternative lasers might also be used. Hence, although an excimer laser is the illustrative source of an ablating beam, other lasers may be used in the present invention.

Laser 12 and delivery optics 16 will generally direct laser beam 14 to the eye E of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In some embodiments, both laser 14 and the laser delivery optical system 16 will be under computer control of processor system 22 to effect the desired laser sculpting process, with the processor system effecting (and optionally modifying) the pattern of laser pulses. In some embodiments, a treatment plan is developed to treat a layer of tissue, and the treatment plan can be defined with a pattern of laser beam pulse. For example, a treatment plan to ablate the epithelial layer may comprise a pattern of laser beam pulses applied to the epithelial layer, and a treatment plan to ablate the stromal tissue may comprise a pattern of stromal laser beam pulses applied to the stromal layer. The pattern of pulses may by summarized in machine readable data of tangible media 29 in the form of a treatment table. The treatment table may be adjusted according to feedback input into processor system 22 from an automated image analysis system (manually input into the processor system by a system operator) in response to feedback data provided from an ablation monitoring system feedback system. Such feedback might be provided by integrating the wavefront measurement system described below with the laser treatment system 10, and processor system 22 may continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892. The laser beam may also be tailored by varying the size and offset of the laser spot from an axis of the eye, as described in U.S. Pat. Nos. 5,683,379, and 6,203,539.

Still further alternatives are possible, including scanning of the laser beam over a surface of the eye and controlling the number of pulses and/or dwell time at each location, as described, for example, by U.S. Pat. No. 4,665,913; using masks in the optical path of laser beam 14 which ablate to vary the profile of the beam incident on the cornea; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791. An ablation effluent evacuator/filter, and other ancillary components of the laser surgery system which are not necessary to an understanding of the invention, need not be described in detail for an understanding of the present invention.

Processor system 22 may comprise (or interface with) a conventional PC system including the standard operator interface devices such as a keyboard, a display monitor, and the like. Processor system 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, or the like, and the processor system 22 will include the memory boards and other standard components of modern computer systems for storing and executing this code. Tangible storage media 29 may optionally embody wavefront sensor data, wavefront gradients, a wavefront elevation map, a treatment map, a corneal topography map, a measurement of refraction of the eye, pupil images of the eye such as iris registration data, epithelial map data, and/or an ablation table.

FIG. 1B illustrates profiles of mapped tissue structures of an eye, according to embodiments of the present invention. An eye E comprises an epithelium or epithelial layer, Bowman's membrane, a stroma/stromal layer under Bowman's membrane, and an endothelial layer. As Bowman's membrane is substantially collagenous and has a poorly defined posterior boundary with the stromal layer, at least a portion of Bowman's membrane can be considered a part of the stromal layer in some embodiments of the present invention. Eye E includes an iris that defines a pupil. The epithelial thickness above the stromal layer and Bowman's membrane is mapped and has as a central thickness E1 and a peripheral thickness E2. In some embodiments, several thickness measurements are made along a tissue section to profile the thickness along the section, and several sections measured to provide a map of epithelial thickness along two dimensions over the pupil of the eye. In some embodiments, several OCT scans are made along tissue sections to map the epithelium. In some embodiments, Scheimpflug images are measured along tissue sections and combined to make a three dimensional map. The maps can be shown as three dimensional maps of corneal thickness with the first two dimensions corresponding to transverse positions on the eye and the third dimension corresponding to the thickness of the epithelial layer at locations along the first two dimensions. In some embodiments, the thickness of additional structures are mapped, for example thickness of the stromal layer defined by a distance from Bowman's membrane to the endothelial layer, a thickness of the crystalline lens and/or a length of the eye.

Figure 1C:
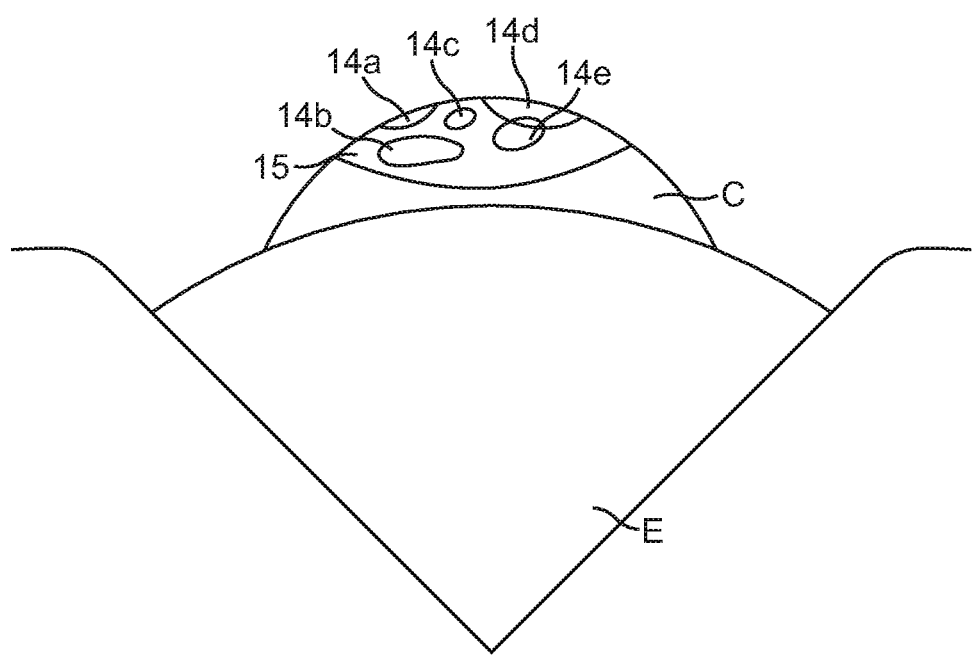
FIG. 1C illustrates an ablation of a region of a cornea of an eye using an arrangement of scanning laser beam pulses of varying diameter applied over a region of a cornea of an eye, according to embodiments of the present invention.

An ablation of a region of a cornea of an eye using an arrangement of pulses 14a-14e of a scanning laser beam is illustrated in FIG. 1C. The arrangement of pulses is applied to positions over a region 15 of a cornea C of an eye E. As illustrated in FIG. 1A, pulses 14e and 14d overlap. A dimension across pulse 14c is smaller than a dimension across pulse 14b. The arrangement of pulses 14a to 14e corresponds to the coordinate position and size of each pulse. The arrangement can be ordered to define a sequential series of pulses 14a to 14e that is sequentially applied to eye E in accordance with a treatment table listing. The treatment table lists the coordinates and sizes of the laser beam for each pulse. Mathematically, an arrangement of pulses in a treatment table may correspond to a pulse instruction vector (hereinafter "PIV") that represents the laser instruction for each pulse. Systems and methods for determining an arrangement of laser beam pulses with basis functions are described in U.S. Pat. No. 7,008,415, the full disclosure of which is incorporated herein by reference.

A sequential series of pulses that ablates the epithelial layer to a desired shape can be referred to as an epithelial series of pulses. In some embodiments, an epithelial series of pulses can be used to ablate the epithelial layer, for example to provide access to at least one of the stromal layer or Bowman's membrane. The epithelial series of pulses may be arranged to ablate the epithelial layer in response to the mapped thickness of the epithelial layer.

An additional ablation procedure can then be ablated into at least one of the stromal corneal tissue or Bowman's membrane to provide a refractive correction with a stromal arrangement of pulses. A sequential series of pulses that ablates the stromal layer can be referred to as a stromal series of pulses.

In some embodiments, some of the pulses may simultaneously ablate epithelial tissue and Bowman's membrane and/or stromal tissue, and such pulses may be referred to as crossover pulses. Crossover pulses may occur when the epithelial layer is partially removed and the laser beam pulse irradiates residual epithelial tissue and exposed Bowman's membrane tissue and/or stromal tissue with the same pulse.

As the corneal stroma, like the Bowman's membrane, includes substantially acellular collagenous tissue and collagenous tissue fibers, ablation of Bowman's membrane can be modeled with stromal ablation basis functions. Also, in some embodiments, Bowman's membrane may comprise a thickness of two to three microns such that modeling of Bowman's tissue as stromal tissue may have a minimal impact on error in the ablated shape.

In some embodiments, the epithelial layer can be ablated with epithelial pulses until penetration of the stroma is detected with crossover epithelial pulses that simultaneously ablate epithelial tissue and Bowman's tissue and/or stromal tissue, and the operator may pause the treatment. The treatment can be resumed with stromal pulses and the stromal layer can be subsequently ablated with stromal pulses. The epithelium may be allowed to grow back over the stroma following stromal ablation with stromal pulses.

The treatment table can be sorted in many ways. In some embodiments, the epithelial series of pulses is applied to the epithelial layer and the stromal series of pulses applied to the stromal layer. In some embodiments, the pulses are sorted such that some of the pulses from the stromal series are applied to the epithelial layer and some of the pulses from the epithelial series are applied to the stromal layer. The stromal pulses may be combined with the epithelial pulses such that the stromal pulses are interspersed, or mixed, between the epithelial pulses by sorting, such that many epithelial pulses are applied to the stromal tissue layer after the epithelial layer is ablated and many stromal pulses are applied to the epithelial layer before the stromal layer is ablated.

In some embodiments, the epithelium and stroma can be ablated to remove corneal haze with minimal intended impact on the refraction of the eye.

Figure 2:
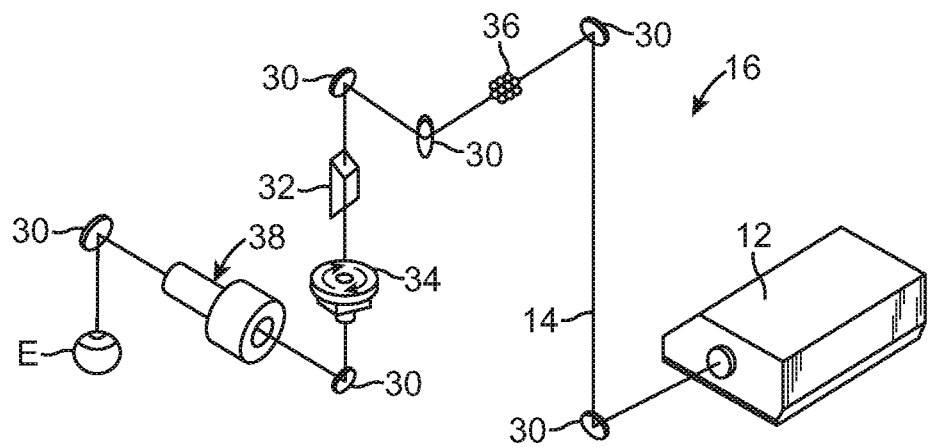
FIGS. 2 and 3 schematically illustrate a laser beam delivery system for selectively directing a laser beam onto the corneal tissue, according to embodiments of the present invention.

Referring now to FIG. 2, laser beam delivery system 16 for directing laser beam 14 at eye E will often include a number of mirrors 30, as well as one or more beam homogenizers. The laser beam homogenizers can even (or otherwise tailor) the laser energy distribution across the laser beam with spatial and temporal integration. Spatial integration can include overlapping portions of the laser beam with prisms, diffractive optics, lenses and the like. In some embodiments, a hexagonal array of prisms 36 separates laser beam 14 into a plurality of beamlets, which may partially overlap on eye E to smooth edges of the ablation or "crater" from each pulse of the laser beam. Temporal integration can include moving the beam, for example with rotation with dove prisms, K-mirrors, cylindrical lens pairs and the like. In some embodiments, temporal integrator 32, may comprise a dove prism. Laser 12 will often comprise an excimer laser as described above. Apparatus for laser beam homogenization are described in U.S. Pat. Nos. 5,646,791; 5,912,775; 816,316 and 7,206,132.

In some embodiments, a variable aperture 34 changes a diameter and/or slot width profile of laser beam 14. In specific embodiments, the variable aperture includes both a variable diameter iris and a variable width slot. Variable aperture 34 may comprise a variable diameter iris and/or a plurality of apertures on a movable structure such as a plate or wheel. In some embodiments that scan the laser beam over the eye with offset of the laser beam, a variable sized circular aperture may provide correction of astigmatism and wavefront aberrations, optionally without the variable slot.

Figure 3:
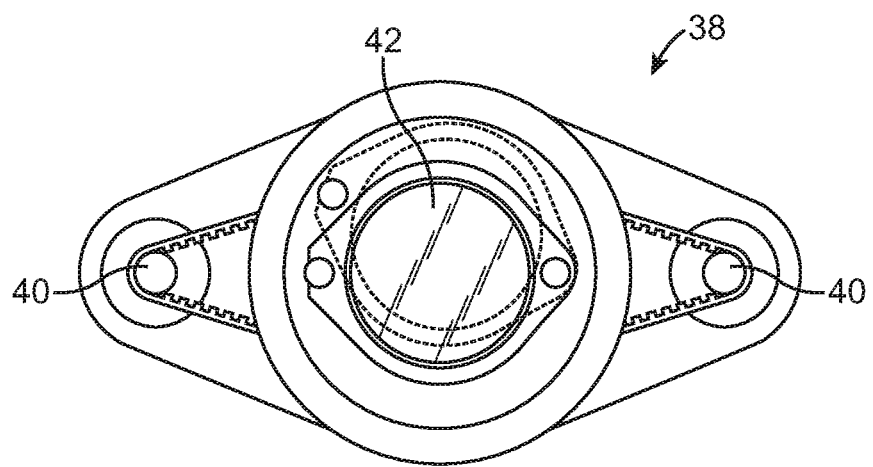

Referring now to FIGS. 2 and 3, an offset module 38 may include motors 40 which vary an angular offset of an offset lens 42, and which also change the radial orientation of the offset. Hence, offset module 38 can selectively direct laser beam 14 at a desired lateral region of the cornea. A structure and method for using laser beam delivery system 16 and offset module 38 are more fully described in U.S. Pat. Nos. 6,984,227; 6,331,177; 6,203,539; 5,912,775; and 5,646,791. In some embodiments, the offset module may comprise scanners with movable mirror that are controlled with galvanometer current measurements, as described in U.S. Pat. Nos. 4,718,418; 4,665,913 and 5,480,396.

Figure 4:
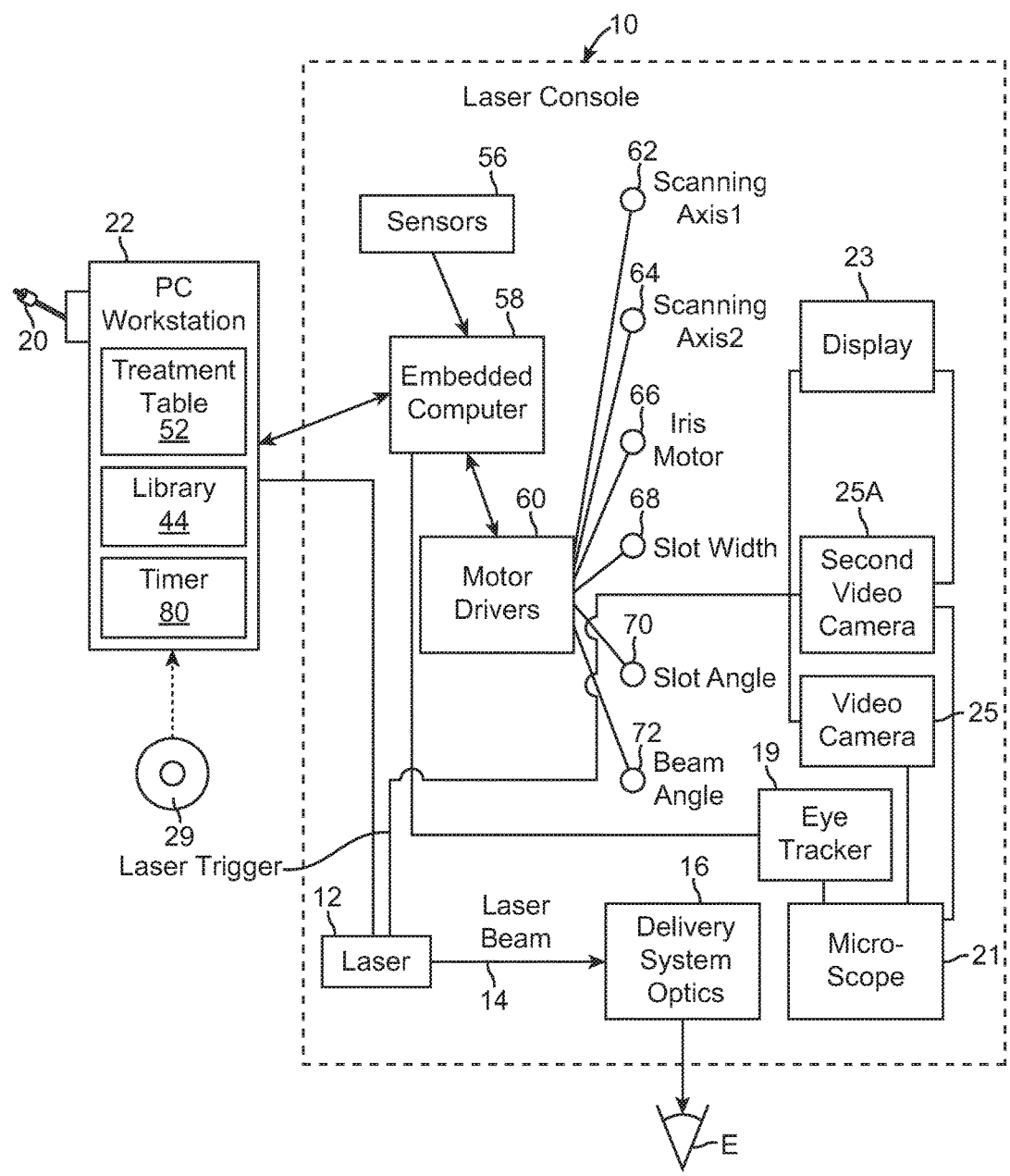
FIG. 4 is a function block diagram illustrating a control architecture of an ablation system as in FIG. 1, according to embodiments of the present invention.

Referring now to FIG. 4, a control system of a laser system 10 is schematically illustrated according to the principles of the present invention. A processor system 22 enables precise control of laser system 10 to sculpt a surface shape specified in a laser treatment table 52. A processor system 22, which generally comprises a PC workstation, makes use of a computer program stored on a tangible media 29 to generate treatment table 52. Processor system 22 may include a library 44 of treatments and treatment tables as described in U.S. Pat. Nos. 6,245,059; and 7,077,838. In some embodiments, processor system 22 may additionally include several basis data profiles and programs to calculate simulated ablation shapes and determine a sequence of laser beam pulses. An embedded computer 58 within laser system 10 is in electronic communication with the PC workstation. Alternatively, a PC workstation may be embedded in the laser system and include an embedded processor card in communication with the PC workstation for directing the ophthalmic surgery. The eye tracker 19, as described above, can be connected to embedded computer 58. Video camera 25 and second video camera 25A can be optically coupled to microscope 21, as described above, and connected to display 23 to show images of the eye to the surgeon and/or system operator.

Embedded computer 58 is in electronic communication with a plurality of sensors 56 and a plurality of motor drivers 60. The motor drivers 60 are coupled to the embedded computer 58 to vary the position and configuration of many of the optical components of the delivery optics 16 according to treatment table 52. For example, first and second scanning axis 62, 64 control the position of the offset lens to move the beamlets over the surface of the cornea. Iris motor 66 controls the diameter of the overall beam, and in some cases, the length of light transmitted through a variable width slot. Similarly slot width driver 68 controls the width of the variable slot. Slot angle driver 70 controls rotation of the slot about its axis. Beam angle driver 72 controls rotation of the beam as effected by a temporal integrator as described above. Processor system 22 issues a command for laser 12 to generate a pulse of the laser beam 14 after the various optical elements have been positioned to create a desired crater on eye E. Treatment table 52 comprises a listing of all of the desired craters to be combined so as to effect a treatment therapy.

A timer 80 may be located on an add on card of processor system 22 and in some embodiments may comprise a Lab-PC-1200 model card having timers 8253/8254. The Lab-PC-1200 model card is available from National Instruments of Austin, Tex. In alternate embodiments, timer 50 is located externally to processor system 22. The timer 80 is controlled by a computer program of processor system 22 and is adapted to measure time intervals. The laser 12 is electronically coupled to processor system 22. Laser 12 fires upon a command issued from processor system 22 in response to a time interval measured by timer 80. Processor system 22 varies the rate at which laser 62 fires during at least a portion of a treatment of an eye E.

Figure 5A:
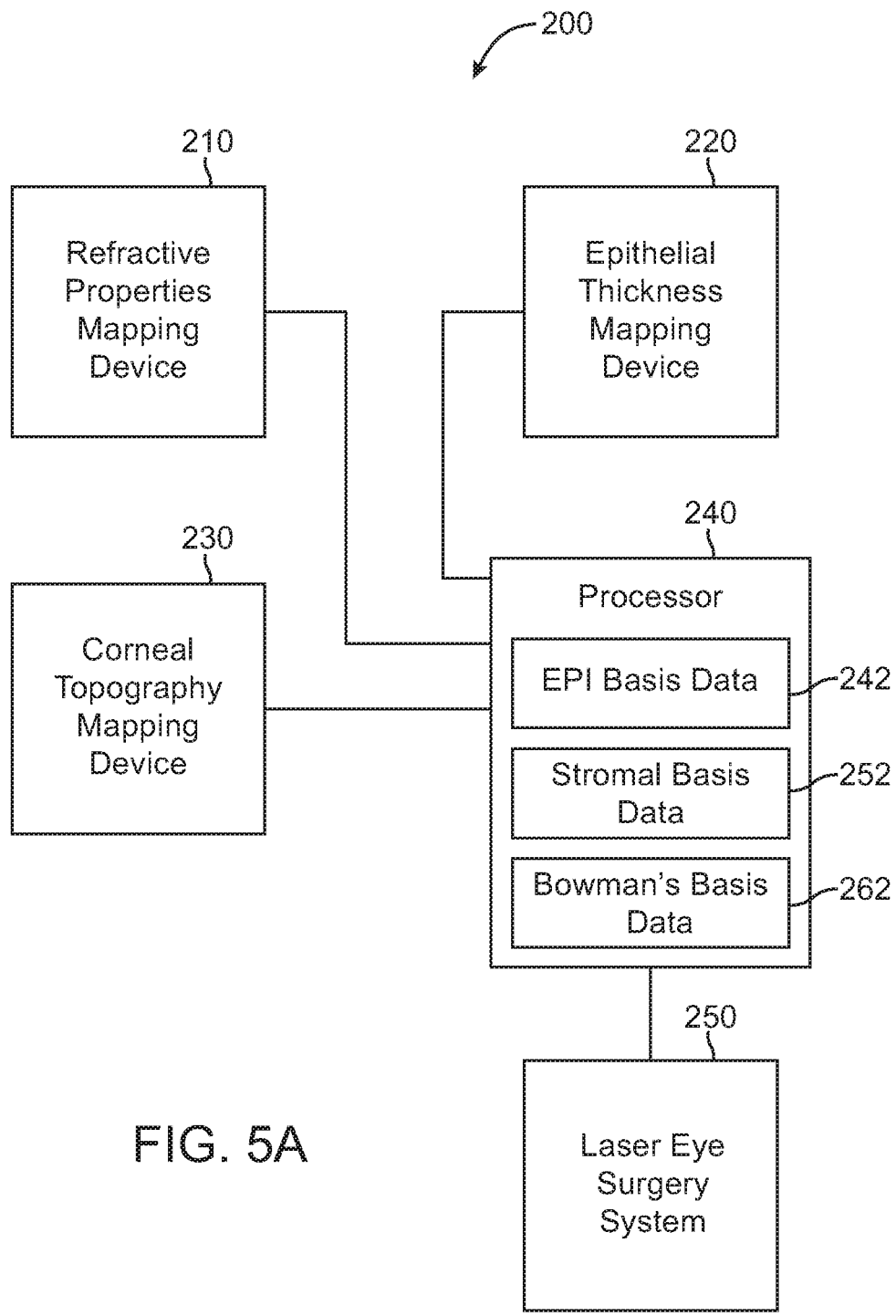
FIG. 5A is a schematic illustration of a system for mapping refractive optical properties of an eye, mapping epithelial thickness of the eye, and ablating the eye with an arrangement of laser beam pulses, according to embodiments of the present invention.

FIG. 5A is a schematic illustration of a system 200 for mapping refractive optical properties of an eye, mapping epithelial thickness of the eye, and ablating the eye with an arrangement of laser beam pulses, according to embodiments of the present invention. System 200 includes a refractive properties mapping device 210. Refractive properties mapping device 210 can map refractive optical properties of the eye, for example wavefront elevation mapping of the refractive properties of the entire optical train of the eye extending from the cornea to the retina. System 200 includes an epithelial thickness mapping device 220. Epithelial thickness mapping device 220 maps a thickness of the epithelial layer covering Bowman's membrane and the stroma. System 200 may include a corneal topography mapping device 230. Corneal topography mapping device 230 maps a surface topography of the front surface of the cornea, for example with videokeratography. In some embodiments, system 200 includes the same device to perform both corneal epithelial mapping and corneal topography mapping.

System 200 includes a processor system 240, with many of the components as described above. Processor system 240 includes epithelial basis data 242, stromal basis data 252 and may comprise Bowman's basis data 262. Epithelial basis data 242 includes ablation profiles for laser beam pulses to the epithelial layer that can be used to calculate the shape of tissue removed from the epithelial layer for an epithelial arrangement of laser beam pulses applied to the epithelial layer. Stromal basis data 252 includes ablation profiles for laser beam pulses to the stromal layer that can be used to calculate the shape of tissue removed from the stromal layer with a stromal arrangement of laser beam pulses applied to the stromal layer. Bowman's basis data 252 includes ablation profiles for laser beam pulses to Bowman's layer that can be used to calculate the shape of tissue removed from Bowman's layer with a Bowman's arrangement of laser beam pulses applied to Bowman's layer. System 200 includes a laser eye surgery system 250. Laser eye surgery system 250 can include many of the components described above.

Processor system 240 receives as input mapped epithelial thickness profile data from device 220, and mapped refractive property profile data from device 210. Processor system 240 can receive input from many additional sources to determine the treatment for the patient, for example patient manifest refraction, age and keratometry. Processor system 240 uses the epithelial, stromal and/or Bowman's basis profile data to determine the arrangement of laser beam pulses, for example as a pulse instruction vector as described in U.S. Pat. No. 7,008,415, the full disclosure of which has been previously incorporated herein by reference. Processor system 240 outputs a laser treatment table to laser eye surgery system 250. The laser eye surgery system uses coordinate references in the treatment table and sizes of the laser beam to treat the eye.

In some embodiments, processor system 240 may comprise a distributed processor network that includes a plurality of processors in electronic or other communication, for example of the Internet, an intranet and/or local area network with wireless communication. In specific embodiments, an operator can carry a floppy drive from one processor to another processor to effect communication among the processors of the processor system. In some embodiments, refractive properties mapping device 210 comprises a processor; epithelial thickness mapping device 220 comprises a processor; and corneal topography mapping device 230 comprises a processor and laser eye surgery system 250 comprises a processor. Processor system 240 may comprise the processors of any of the measurement devices and the laser eye surgery system.

Refractive properties mapping device 210 may comprise many devices that can be used to determine the refractive properties of the optical path of the eye from the front surface of the cornea to the retina with subjective and/or objective measurements. In some embodiments refractive properties mapping device 210 comprises a Hartmann Shack wavefront sensor, for example as described in U.S. Pat. Nos. 6,155,684; 6,264,328; 6,271,914; 6,271,915; and 7,036,934. In some embodiments, refractive properties mapping device 210 comprises a spatially resolved refractometer, for example as described in U.S. Pat. Nos. 5,258,791; 6,000,800; and 6,409,345. In some embodiments, the device to measure the eye may include objective measurements with a light probe beam, for example as described in U.S. Pat. No. 6,409,345, entitled "Method and Device for Synchronous Mapping of the Total Refraction Non-Homogeneity of the Eye and Its Refractive Components"; and U.S. Pat. No. 6,932,475, entitled "Device for Measuring Aberration Refraction of the Eye". In some embodiments, the refractive optical properties of the eye may be measured with an interferometer, for example as described in U.S. Pat. No. 7,084,986, entitled "System for Measuring the Optical Image Quality of an Eye in a Contactless Manner"; and U.S. Pat. No. 6,922,250, entitled "Optical Multiplex Short Coherence Interferometry on the Eye". In some embodiments, the optical property of the eye is measured with an autorefractor, for example as described in U.S. Pat. No. 7,001,020, entitled "Complete Autorefractor System in an Ultra-Compact Package"; and U.S. Pat. No. 5,329,322, entitled "Palm Size Autorefractor and Fundus Topographical Mapping Instrument". The optical property of the eye determined with many of these devices can be determined as a wavefront elevation map, Zernike coefficients, and Fourier coefficients, for example as described in U.S. Pat. No. 6,299,311, entitled "Rapid, Automatic Measurement of the Eye's Wave Aberration; U.S. Pat. No. 7,175,278, entitled "Wavefront Reconstruction Using Fourier Transformation and Direct Integration", and U.S. Pat. No. 7,168,807, entitled "Iterative Fourier Reconstruction for Laser Surgery and Other Optical Applications".

Epithelial thickness mapping device 220 may comprise many devices that can used to determine a thickness of the epithelial layer. In some embodiments, epithelial mapping device 220 measures energy reflected from the interface of the epithelial layer with Bowman's membrane and/or the stroma. The reflected energy may comprise light energy and/or ultrasonic energy. In some embodiments epithelial thickness mapping device 220 comprises an optical coherence tomography (hereinafter "OCT") machine, for example as described in U.S. Pat. Nos. 5,491,524; 6,741,359; and 6,755,819. In some embodiments, the epithelial thickness mapping device may comprise a high frequency ultrasound array, for example as described in U.S. Pat. Nos. 6,315,727; 6,949,071; 7,048,690. Scheimpflug and other photography may also be used to map thickness of the epithelial layer U.S. Pat. Nos. 4,523,821; 5,512,965; 6,286,958; 6,588,903. In some embodiments, epithelial mapping device 220 may comprise a con-focal microscope, for example as described in U.S. Pat. Nos. 5,359,373 and 6,118,580. In some embodiments, epithelial mapping device 220 may measure a thickness of Bowman's membrane, and the thickness data of Bowman's membrane may be communicated within processor system 240 and used to determine an arrangement of laser beam pulses to ablate Bowman's membrane.

In some embodiments, epithelial mapping device 220 comprises an imaging system to image the iris of eye E while the epithelium is mapped. The mapped epithelial thickness profile can then be registered and/or stored with the epithelial thickness profile so as to permit registration of the mapped epithelium with the iris. The registration of the mapped epithelium can occur while the epithelial thickness is mapped and/or during ablation of the region of the eye. Examples of systems and methods to register an image of the iris of the eye during laser ablation are described in U.S. Pat. No. 7,044,602, entitled "Methods and Systems for Tracking a Torsional Orientation and Position of an Eye". In some embodiments, the processor system may adjust the arrangement of laser beam pulses in real time in response to torsional alignment of the eye while the patient is treated with the therapeutic laser beam.

Corneal topography mapping device 230 may comprise many devices that can be used to measure and/or map topography of the corneal surface. In some embodiments corneal topography mapping device 230 can comprise a machine that analyzes images reflected from the eye to determine the topography map of the anterior surface of the cornea as described, for example, in U.S. Pat. Nos. 4,692,003; 4,863,260; 5,062,702; and 5,841,511. In some embodiments, corneal topography mapping device 230 comprises fluorescence that analyzes the position fluorescence from a pattern projected on the eye to determine the shape of the front surface of the eye as described, for example, in U.S. Pat. Nos. 4,761,071; 4,995,716; 5,159,361; 6,592,574; 6,613,041; and 6,666,857.

Figure 5B:
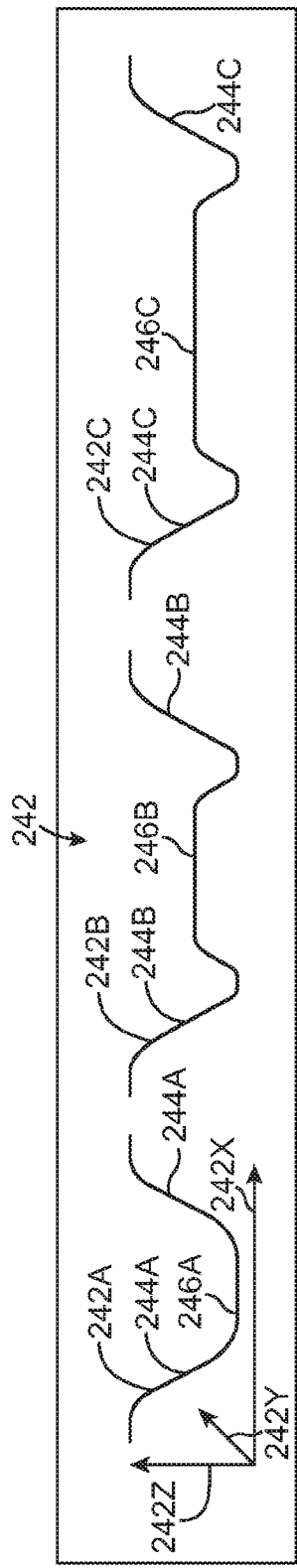
FIG. 5B is a schematic illustration of epithelial basis data used to determine an arrangement of laser beam pulses to ablate an epithelial layer to a targeted epithelial ablation profile, according to embodiments of the present invention.

FIG. 5B is a schematic illustration of epithelial basis data 242 used to determine an arrangement of laser beam pulses to ablate an epithelial layer with an epithelial ablation profile, according to embodiments of the present invention. Epithelial basis data 242 includes profiles of epithelial basis data for small, medium and large beam diameters, for example 2, 4 and 6 mm beam diameters respectively. A coordinate reference system 242X, 242Y, and 242Z show dimensions of the basis ablation profile data. Each of the profiles shows a characteristic ablation for a single pulse of the laser beam at the specified diameter. A peripheral portion of each basis ablation profile corresponds to a concave ablation in tissue and comprises concave surface curvature with localized negative optical power. An inner portion of each basis ablation profile may correspond to a concave, convex or flat localized ablation surface curvature in tissue depending on the size and characteristics of the laser beam and type of tissue ablated. In some embodiments, the inner portion can be concave with concave surface curvature, for example with 1 mm beam diameters and with Gaussian laser beam profiles. In some embodiments with flat top or uniform laser energy distribution laser beams with diameter greater than about 3 mm, the inner portion of the ablation may comprise localized flat and convex surface curvature while the peripheral portion of the ablation comprises localized concave surface curvature. In some embodiments, the inner portion comprises a flat central sub-portion with flat curvature (i.e. no curvature or zero curvature) and a peripheral inner sub-portion with convex curvature.

Small pulse ablation profile 242A illustrates ablation profile data for a small diameter laser beam. Small diameter pulse ablation profile 242A comprises an inner portion 246A and an annular peripheral portion 244A. Annular peripheral portion 244A comprises a concave surface curvature ablated with a peripheral portion of the laser beam. Inner portion 246A comprises a concave surface curvature ablated with a central portion of the laser beam.

Medium pulse ablation profile 242B illustrates a profile for a medium diameter laser beam. Medium diameter pulse ablation profile 242B comprises an inner portion 246B and an annular peripheral portion 244B. Annular peripheral portion 244B comprises a concave surface ablated with a peripheral portion of the laser beam. Inner portion 246B comprises flat and convex surface curvatures ablated with a central portion of the laser beam, and inner portion 246B is ablated to a lesser depth than peripheral portion 244B. Inner portion 246B comprises a central sub-potion with flat curvature and a peripheral convex sub-portion with convex curvature.

Large pulse ablation profile 242C illustrates a profile for a large diameter laser beam. Large diameter pulse ablation profile 242C comprises an inner portion 246C and an annular peripheral portion 244C. Annular peripheral portion 244C comprises a concave surface curvature ablated with a peripheral portion of the laser beam. Inner portion 246C comprises flat and convex surface curvatures ablated with a central portion of the laser beam. Such profiles can be obtained with a uniform laser beam having a top hat energy distribution profile, although many laser beams and energy distributions can be used, for example multi-laser beam energy distribution profiles, for example as described in U.S. Pat. No. 6,984,227. Inner portion 246C comprises a central sub-potion with flat curvature and a peripheral convex sub-portion with convex curvature.

Epithelial basis data 242 can be generated empirically with experimental measurements from patients. For example, the shape of epithelial tissue can be measured in situ with corneal topography on a population of patients who undergo trans-epithelial PRK. For each pulse diameter profile approximately 10 patients are measured. For example, with basis ablation profiles for each of 1, 2, 3, 4, 5 and 6 mm, 10 patients are measured for a total of 60 patients. Basis data for smaller sized laser beams may also be measured. The corneal epithelial layer may be measured prior to laser ablation with mapping as described above. The shape of the front surface of the cornea can be measured intra-operatively prior to ablation, and then measured subsequently during ablation with many of the corneal topography mapping devices described above. The shape of tissue removed with the fixed size laser beam is then measured for each patient to empirically determine the basis data for the fixed laser beam diameter used. The epithelial tissue can then be removed in many ways, for example mechanically and/or chemically and normal PRK performed.

Figure 5C:
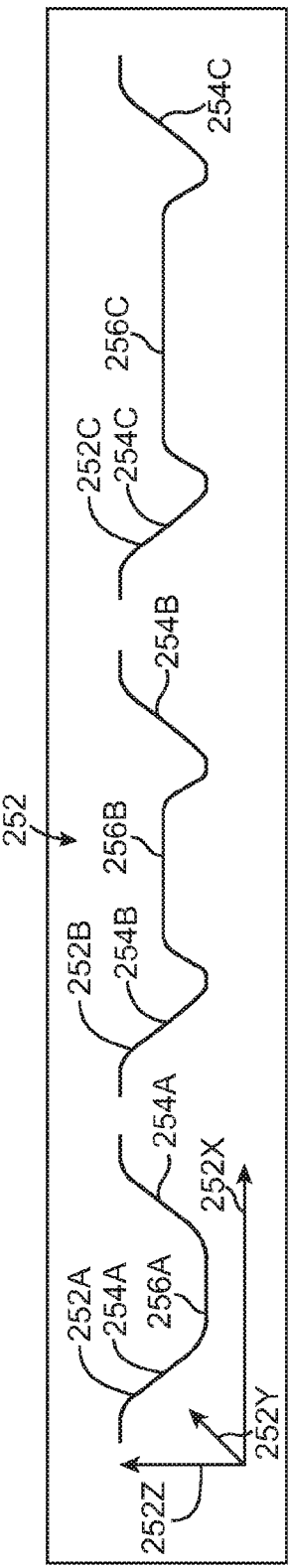
FIG. 5C is a schematic illustration of stromal basis data used to determine an arrangement of laser beam pulses to ablate a stromal layer to a targeted stromal ablation profile, according to embodiments of the present invention.

FIG. 5C is a schematic illustration of stromal basis data 252 used to determine an arrangement of laser beam pulses to ablate a stromal layer with a stromal ablation profile, according to embodiments of the present invention. Stromal basis data 252 can be obtained with many of the laser beams and methods described with respect to the epithelial ablation data. Stromal basis data 252 comprises small diameter pulse ablation profile 252A, medium diameter pulse profile 252B and large diameter pulse profile 252C. In some embodiments the diameters of the small, medium and large diameter pulses are 2, 4 and 6 mm, respectively.

Small pulse ablation profile 252A illustrates ablation profile data for a small diameter laser beam. Small diameter pulse ablation profile 252A comprises an inner portion 256A and an annular peripheral portion 254A. Annular peripheral portion 254A comprises to a concave surface ablated with a peripheral portion of the laser beam. Inner portion 256A comprises a concave surface curvature ablated with a central portion of the laser beam.

Medium pulse ablation profile 252B illustrates a profile for a medium diameter laser beam. Medium diameter pulse ablation profile 252B comprises an inner portion 256B and an annular peripheral portion 254B. Annular peripheral portion 254B comprises a concave surface curvature ablated with a peripheral portion of the laser beam. Inner portion 256B comprises flat and convex surface curvatures ablated with a central portion of the laser beam. Inner portion 256B comprises a central sub-potion with flat curvature and a peripheral convex sub-portion with convex curvature.

Large pulse ablation profile 252C illustrates a profile for a large diameter laser beam. Large diameter pulse ablation profile 252C comprises an inner portion 256C and an annular peripheral portion 254C. Annular peripheral portion 254C comprises a concave surface ablated with a peripheral portion of the laser beam. Inner portion 256C comprises flat and convex surface curvatures ablated with a central portion of the laser beam. Inner portion 256B comprises a central sub-potion with flat curvature and a peripheral convex sub-portion with convex curvature.

In some embodiments, the basis profiles for the epithelial layer and stromal layer are different for the similar beam diameters. For example, the central depth of ablation can be different, and the size of the inner portion flat and convex curvatures may be different.

Figure 5D:
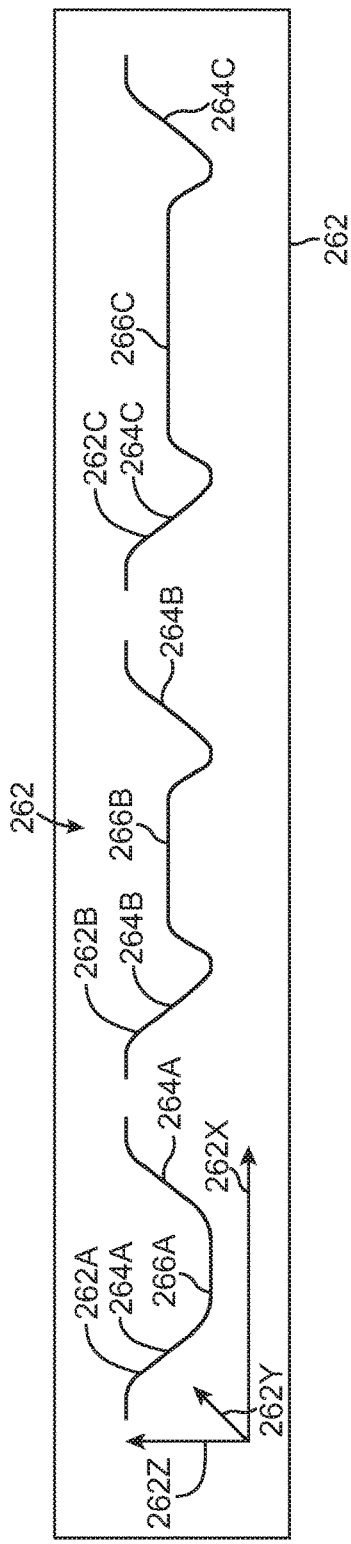
FIG. 5D is a schematic illustration of Bowman's basis data used to determine an arrangement of laser beam pulses to ablate Bowman's layer to a targeted stromal ablation profile, according to embodiments of the present invention.

FIG. 5D is a schematic illustration of Bowman's basis data 262 used to determine an arrangement of laser beam pulses to ablate a stromal layer with a stromal ablation profile, according to embodiments of the present invention. Bowman's basis data 252 can be obtained with many of the laser beams and methods described with respect to the epithelial and stromal ablation data. Bowman's basis data 262 comprises small diameter pulse ablation profile 262A, medium diameter pulse profile 262B and large diameter pulse profile 262C. In some embodiments the diameters of the small, medium and large diameter pulses are 2, 4 and 6 mm, respectively.

Small pulse ablation profile 262A illustrates ablation profile data for a small diameter laser beam. Small diameter pulse ablation profile 262A comprises an inner portion 266A and an annular peripheral portion 264A. Annular peripheral portion 264A comprises to a concave surface ablated with a peripheral portion of the laser beam. Inner portion 266A comprises a concave surface curvature ablated with a central portion of the laser beam.

Medium pulse ablation profile 262B illustrates a profile for a medium diameter laser beam. Medium diameter pulse ablation profile 262B comprises an inner portion 266B and an annular peripheral portion 264B. Annular peripheral portion 264B comprises a concave surface curvature ablated with a peripheral portion of the laser beam. Inner portion 266B comprises flat and convex surface curvatures ablated with a central portion of the laser beam. Inner portion 266B comprises a central sub-potion with flat curvature and a peripheral convex sub-portion with convex curvature.

Large pulse ablation profile 262C illustrates a profile for a large diameter laser beam. Large diameter pulse ablation profile 262C comprises an inner portion 266C and an annular peripheral portion 264C. Annular peripheral portion 264C comprises a concave surface ablated with a peripheral portion of the laser beam. Inner portion 266C comprises flat and convex surface curvatures ablated with a central portion of the laser beam. Inner portion 266B comprises a central sub-potion with flat curvature and a peripheral convex sub-portion with convex curvature.

In some embodiments, the basis profiles for the epithelial layer, stromal layer and Bowman's layer are different for the similar beam diameters. For example, the central depth of ablation can be different, and the size of the inner portion flat and convex curvatures may be different for each of the three tissue layers.

FIG. 5E is a schematic illustration of a target epithelial ablation profile 270 and an estimated epithelial ablation profile 272 determined by combining the epithelial basis data with an epithelial arrangement of laser beam pulses, according to embodiments of the present invention. Target epithelial ablation profile 270 can be obtained in many ways; for example, by mapping the epithelium as described above, or by an operator inputting a desired depth of ablation for a uniform epithelial thickness. The processor system then uses the target ablation shape and the epithelial basis data profiles to determine an arrangement of laser beam pulses that will remove tissue to the target profile 270. The processor system combines the arrangement of laser beam pulses with the profile of each laser beam pulse and adds the profiles for each pulse together to obtain the estimated epithelial ablation profile 272. Although the estimated ablation profile 272 can be obtained in many ways, in an embodiment the estimated ablation profile is calculated by adding the epithelial ablation basis profile for each pulse of the treatment together with the other pulses of the treatment to determine the estimated ablation depth 272. The arrangement of laser beam pulses for a given set of epithelial basis data and target ablation shape can be calculated many ways, for example with techniques similar to those described in U.S. Pat. No. 7,008,415, the whole disclosure of which has been previously incorporated herein by reference.

FIG. 5F is a schematic illustration of a target stromal ablation profile 280 and an estimated stromal ablation profile 282 determined by combining the stromal basis data with a stromal arrangement of laser beam pulses, according to embodiments of the present invention. Target stromal ablation profile 280 can be defined in many ways, for example, with wavefront elevation mapping of the refractive error along the optical path of the eye, manifest refraction of the eye, cycloplegic refraction of the eye, and autorefractor refraction of the eye. The processor system uses the target stromal ablation profile and the stromal basis profiles as described above to determine an arrangement of laser beam pulses to ablate the stromal tissue to the target stromal ablation profile 280. Estimated stromal ablation profile 282 can be determined by combining the arrangement of laser beam pulses. For example, a calculation that uses the arrangement of laser beam pulses and the basis data for the stroma can be used to determine estimated stromal ablation profile 282. The processor system may calculate the arrangement of laser beam pulses comprised in a treatment table in many ways; for example, with iterations using the treatment table to determine the arrangement of pulses so that a minimal residual error results between the target ablation profile and estimated ablation profile. Systems and methods for calculating a treatment table with basis data for a target ablation shape are described in U.S. Pat. No. 7,008,415, the full disclosure of which has been previously incorporated herein by reference. In some embodiments, localized laser ablation characteristics based on corneal topography mapping can be used and the treatment table calculated in response to corneal topography, for example as described in U.S. Pat. No. 7,083,609.

Figure 5G:
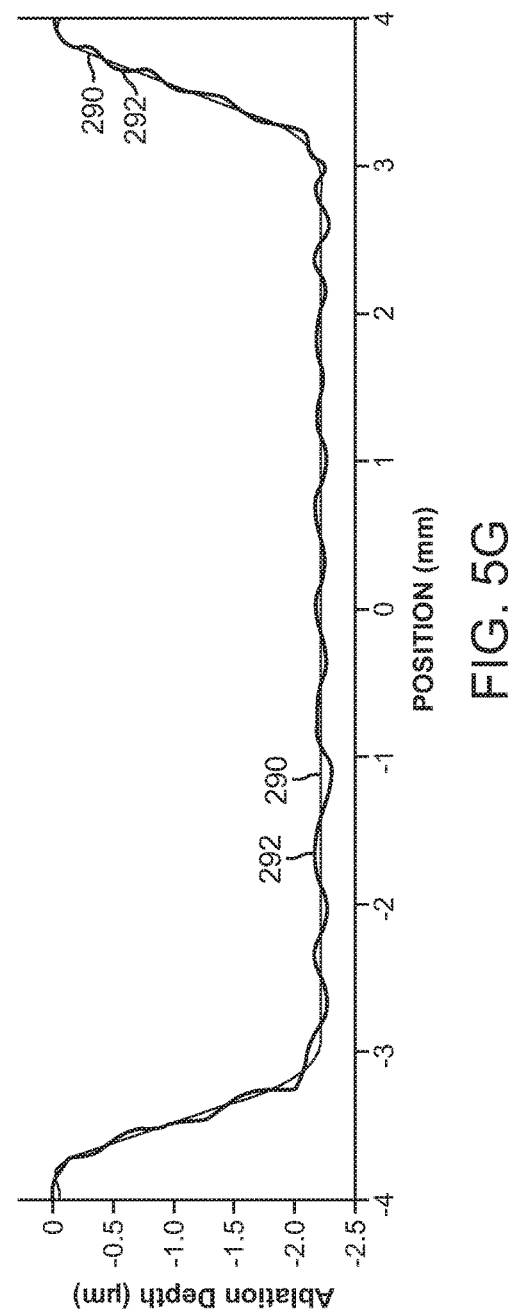
FIG. 5G is a schematic illustration of a target Bowman's ablation profile and an estimated Bowman's ablation profile determined by combining the Bowman's basis data with a Bowman's arrangement of laser beam pulses, according to embodiments of the present invention.

FIG. 5G is a schematic illustration of a target Bowman's ablation profile 290 and an estimated Bowman's ablation profile 292 determined by combining the Bowman's basis data with a Bowman's arrangement of laser beam pulses, according to embodiments of the present invention. Target Bowman's ablation profile 290 can be obtained in many ways; for example, by measuring Bowman's with a confocal microscope as described above, or by an operator inputting a desired depth of ablation through Bowman's membrane. The processor system then uses the target ablation shape and the Bowman's basis data profiles to determine an arrangement of laser beam pulses that will remove tissue to the target profile 290. The processor system combines the arrangement of laser beam pulses with the profile of each laser beam pulse and adds the profiles for each pulse together to obtain the estimated Bowman's ablation profile 272. Although the estimated ablation profile 272 can be obtained in many ways, in an embodiment the estimated ablation profile is calculated by adding the epithelial ablation basis profile for each pulse of the treatment together with the other pulses of the treatment to determine the estimated ablation depth 292. The arrangement of laser beam pulses for a given set of epithelial basis data and target ablation shape can be calculated many ways, for example with techniques similar to those above.

Figure 6A:
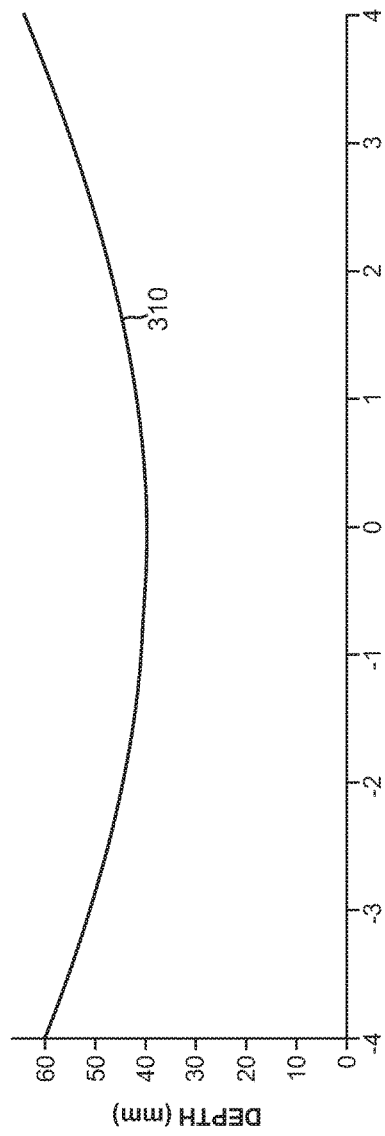
FIG. 6A is a schematic illustration of a profile map of corneal epithelial thickness, according to embodiments of the present invention.

FIG. 6A is a schematic illustration of a mapped profile 310 of corneal epithelial thickness, according to embodiments of the present invention. Map profile 310 shows a depth or thickness of the corneal epithelial layer in microns across the corneal surface from −4 mm to +4 mm referenced in relation to the pupil of the eye. Mapped profile 310 shows the profile along one cross sectional slice of the corneal epithelial layer. In some embodiments, several parallel and perpendicular slices are obtained and the thickness of the epithelial layer is mapped along two dimensions of the eye. In some embodiments, the thickness of the epithelial layer can be three dimensional with two position dimensions along a pupil and/or cornea of the eye and a third dimension corresponding to thickness of the epithelium along the optical axis of the eye through the pupil.

Figure 6B:
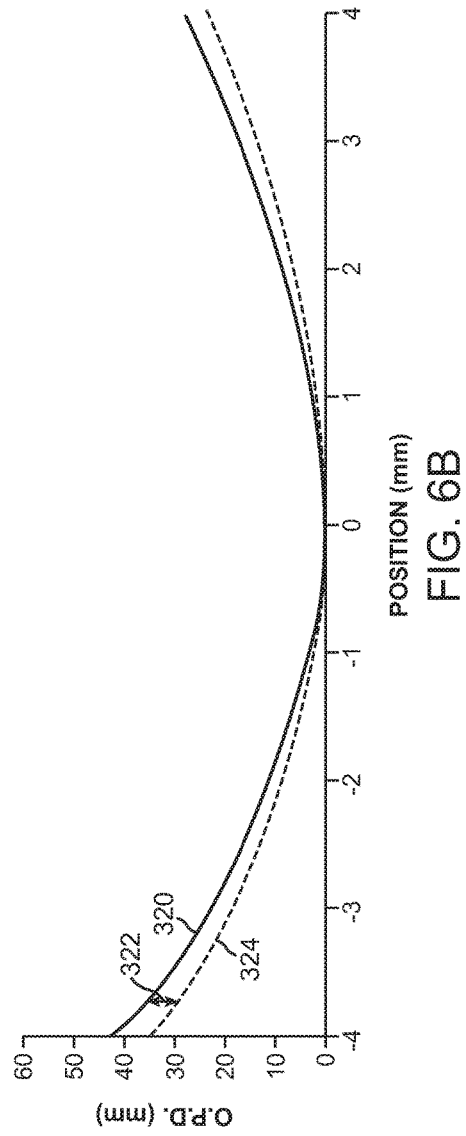
FIG. 6B is a schematic illustration of a profile map of refractive optical properties of the eye, according to embodiments of the present invention.

FIG. 6B is a schematic illustration of a wavefront map profile 320 of refractive optical properties of the eye, according to embodiments of the present invention. Profile 310 can be obtained in many ways including a wavefront mapping device that maps optical path difference or error across the pupil in relation to a plane wave. Epithelial thickness profile 310 can be subtracted from wavefront map profile 320 after the epithelial profile has been converted to optical path length. In some embodiments, the epithelial profile can be converted to optical path length by multiplying the profile by the quantity (n−1) where n is the index of refraction of the epithelium, about 1.377. The optical path length can then be converted to optical path difference (hereinafter "OPD") relative to a plane by subtracting piston, or other constant, from the optical path length such that the epithelial contribution to the refractive optical characteristic is determined. Epithelial contribution 322 can then be subtracted from wavefront map profile 320 to obtain a remainder portion 324. In some embodiments, remainder portion 324 corresponds to curvature of the cornea, refractive power of the lens, and optical path length of the eye along the axis of the eye and the relative positions of the cornea, lens and retina along the optical path length of the eye.

FIG. 6C is a schematic illustration of a stromal ablation profile 330 to correct refractive optical properties of the eye in response to the refractive optical properties profile map as in FIG. 6B, according to embodiments of the present invention. Stromal ablation profile 330 can be calculated from wavefront map profile 320. Stromal ablation profile 330 includes remainder portion profile 334. Remainder portion profile 334 corrects the wavefront error of remainder portion 324. Epithelial contribution profile 332 corrects epithelial contribution 322 to the wavefront map profile 320. In some embodiments, the epithelial layer may heal over the ablation with the post-operative thickness profile the same as the pre-operative thickness profile, such that ablation of the stromal layer to correct epithelial contribution 322 can provide correction of the refractive optical properties of the eye. Hence, ablation of the epithelial contribution and remainder contribution can correct the optical errors of the eye.

In some embodiments, healing of the epithelial layer and stromal layer can affect the final shape of the eye and optical correction that the patient receives. Adjustment to the ablation profile in response to estimated healing may be used.

Figure 6D:
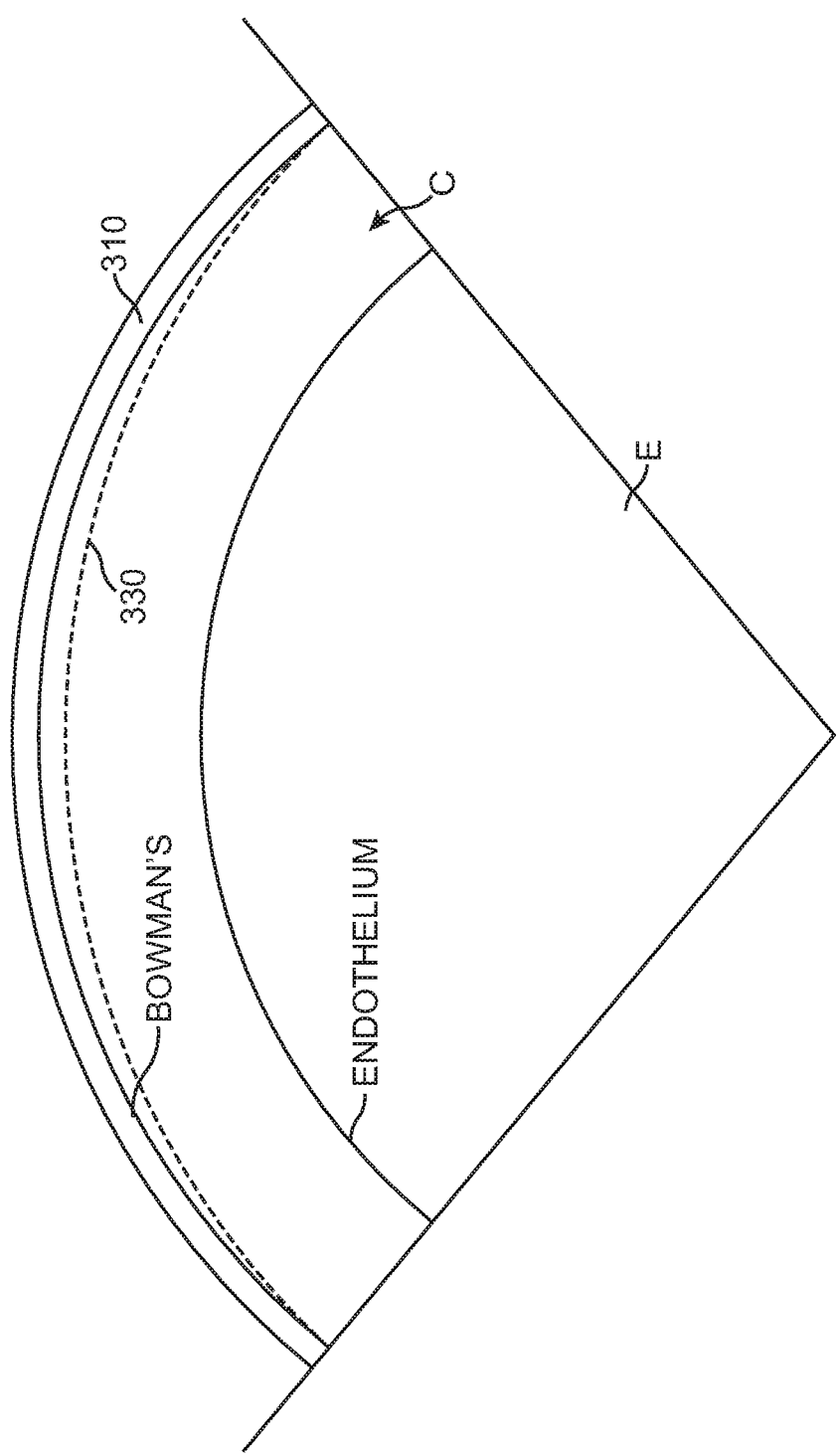
FIG. 6D is a schematic illustration of layers of corneal tissue ablated based on mapping the thickness of the epithelium and mapping the refractive optical properties of the eye, according to embodiments of the present invention.

FIG. 6D is a schematic illustration of layers of corneal tissue ablated based on mapping the thickness of the epithelium and mapping the refractive optical properties of the eye, according to embodiments of the present invention. Stromal ablation profile 330 is shown subtracted from the anterior stromal surface and/or Bowman's surface of the corneal. Epithelial thickness profile 310 is shown over the surface of the cornea. One will appreciate that in some embodiments the epithelial profile 310 will heal following ablation in the stromal layer of profile 330, and thickness profile 310 postoperatively will be changed in some embodiments.

Figure 7A:
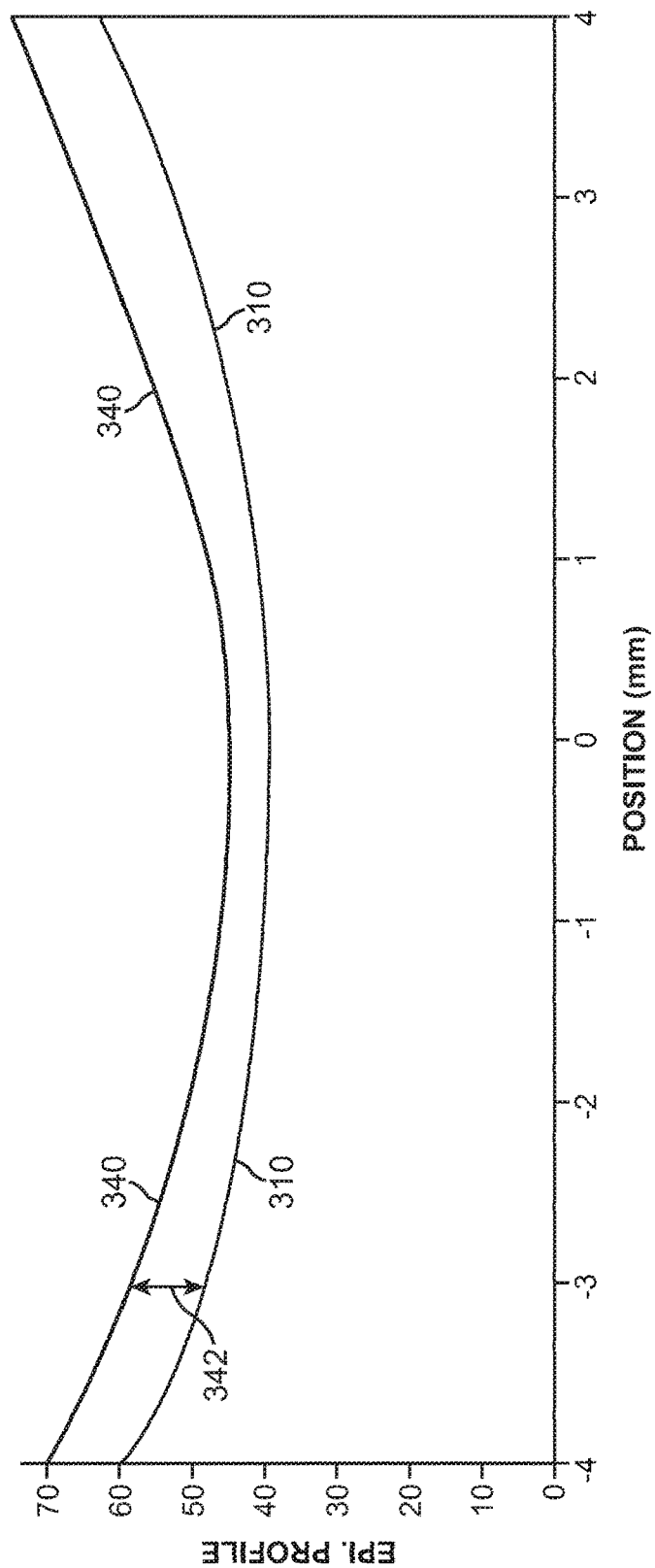
FIG. 7A is a schematic illustration of a profile map of estimated healed corneal epithelial thickness following ablation of the profile map to correct refractive optical properties of the eye, according to embodiments of the present invention.

FIG. 7A is a schematic illustration of a healed epithelial profile 340 of healed corneal epithelial thickness following ablation of the profile map to correct refractive optical properties of the eye, according to embodiments of the present invention. Healed epithelial profile 340 is shown in relation to mapped epithelial profile 310. A change in profile 342 shows the change in pre-operative epithelial profile 310 to post-operative epithelial profile 340. Healed profile 340 and change in profile 342 and can be estimated based on empirical measurements of a patient population of patients who are treated. For example, a patient sample size of 100 patients can be selected and their epithelial thickness measured preoperatively and postoperatively to determine an estimate of postoperative thickness and/or change in thickness of the epithelial layer based on the pre-operative epithelial thickness mapping and ablation characteristics. An estimate of healed epithelial profile 340 can be used to modify the stromal ablation profile to determine an adjusted stromal ablation profile. The estimated healed profile can be in response to several patient variables, for example age, degree of myopia, degree hyperopia, degree of astigmatism, race and sex. The patient population can be increased or decreased as appropriate, depending on the number of variables and level of statistical significance and power.

Similar measurements and estimates can be made for stromal healing based on empirical data, and an estimated healed stromal profile determined. In some embodiments, the front surface of the stromal layer and/or Bowman's membrane is determined, for example by subtracting the mapped epithelial thickness profile from a corneal topography measurement. Pre-operative corneal topography measurements and post-operative corneal topography measurements can be made when the epithelial layer is mapped as described above, such that the stromal profile can be determined from the corneal topography and mapped epithelial layer. The stromal ablation profile can be adjusted in response to the changes in stromal profile and/or epithelial profile.

FIG. 7B is a schematic illustration of an adjusted stromal ablation profile 350 in response to the map of estimated corneal epithelial thickness following ablation as in FIG. 7A, the profile map of corneal epithelial thickness as in FIG.

6A, and the profile map of refractive optical properties of the eye as in FIG. 6B, according to embodiments of the present invention. Adjusted stromal ablation profile 350 includes a healed epithelial contribution 352 and remainder portion profile 334. For comparison, stromal ablation profile 330 without the healing adjustment is also shown. Remainder portion profile 334 can be added to healed epithelial profile contribution 352 to obtain adjusted stromal ablation profile 350. Adjusted stromal ablation profile 350 can then be used as a target stromal ablation profile and the arrangement of laser beam pulses solved to ablate the stroma with this profile.

Figure 8A:
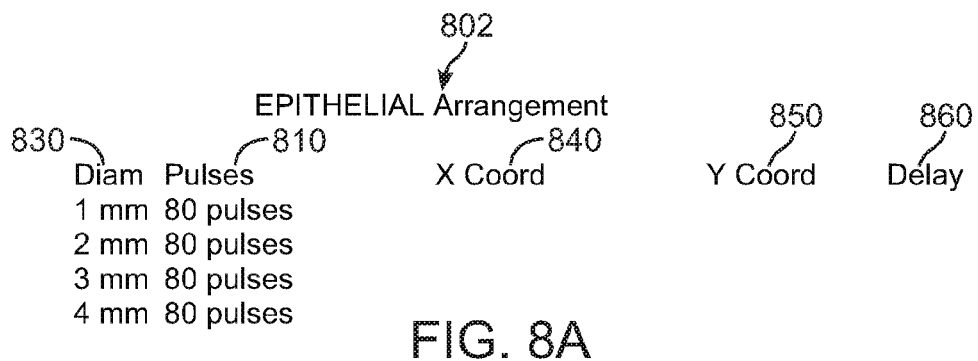
FIG. 8A is a simplified schematic illustration of an epithelial arrangement of pulses in accordance with embodiments of the present invention.

FIG. 8A is a simplified schematic illustration of an epithelial arrangement 802 of pulses in accordance with embodiments of the present invention. Epithelial arrangement 802 includes a diameter 830, an x-coordinate 840, y-coordinate 850 and a delay 860 for each pulse of the arrangement. A number of pulses 810 for each diameter and/or pulse number can also be specified for each pulse of the arrangement. A treatment table with delays, positions and diameters sorted to avoid tissue heating is described, for example, in U.S. Pat. No. 7,077,838. An illustrative epithelial treatment for epithelial mapping treatments may include 80 pulses of 1 mm diameter, 80 pulses of 2 mm diameter, 80 pulses of 3 mm diameter, and 80 pulses of 4 mm diameter. In some embodiments, each line in the treatment table corresponds to a single pulse of the laser beam, such that each pulse has its own position and delay, and the pulse position and delay can vary within each group of pulses. Although the illustrative embodiment can list positions for each pulse of the laser beam, the arrangement of pulses can be organized as a trajectory, or the like.

Figure 8B:
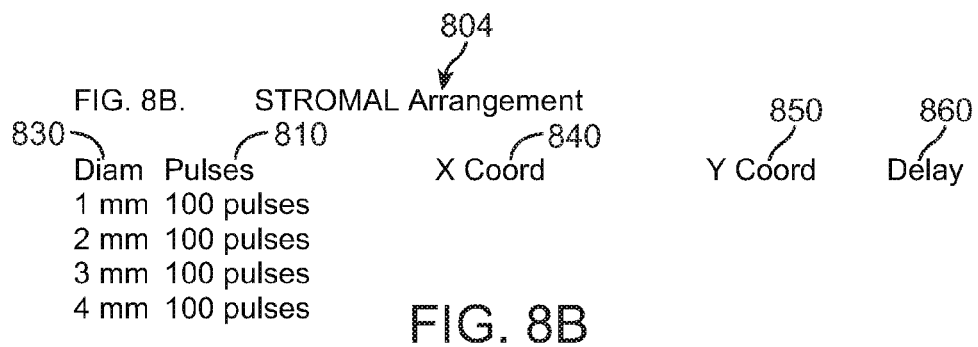
FIG. 8B is a simplified schematic illustration of a stromal arrangement of pulses in accordance with embodiments of the present invention.

FIG. 8B is a simplified schematic illustration of a stromal arrangement 804 of pulses in accordance with embodiments of the present invention. Stromal arrangement 804 includes diameter 830, x-coordinate 840, y-coordinate 850 and delay 860 for each pulse of the arrangement. Number of pulses 810 or pulse number is also be specified for each pulse of the arrangement. An illustrative stromal treatment to correct epithelial and remainder component aberrations may include 100 pulses of 1 mm diameter, 100 pulses of 2 mm diameter, 100 pulses of 3 mm diameter, and 100 pulses of 4 mm diameter.

Figure 8C:
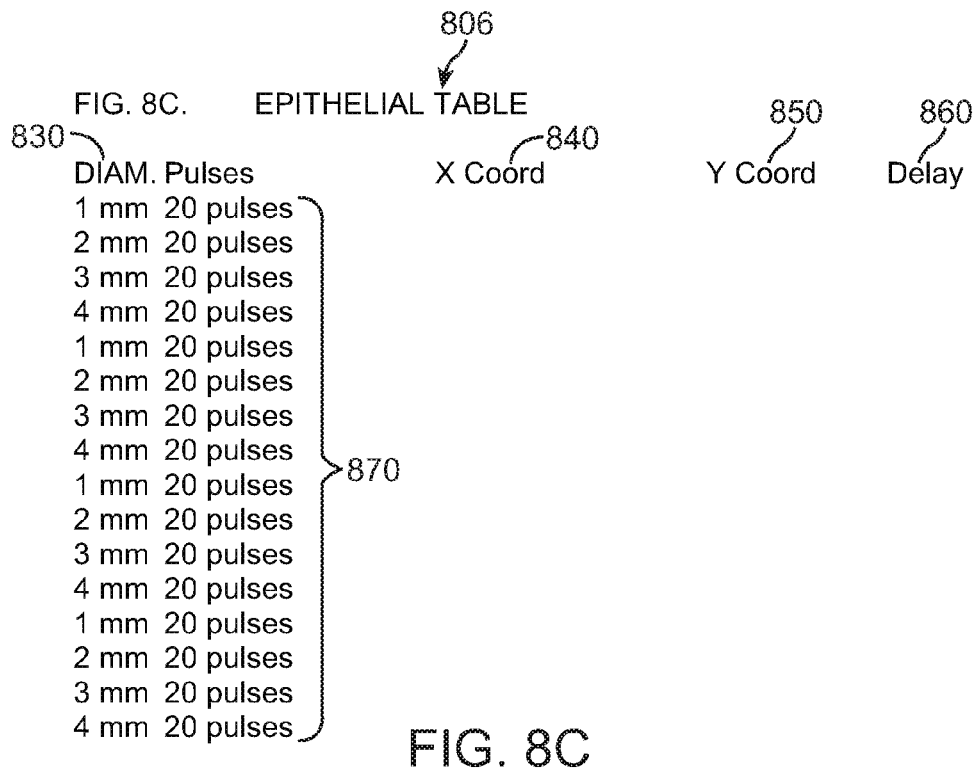
FIG. 8C is a simplified schematic illustration of an epithelial treatment table that comprises epithelial arrangement, according to embodiments of the present invention.

FIG. 8C is a simplified schematic illustration of an epithelial treatment table 806 that comprises epithelial arrangement 802, according to embodiments of the present invention. Epithelial treatment table 806 comprises an epithelial sequence 870 of laser beam pulses, which is determined in response to epithelial mapping as described above. Epithelial arrangement 802 can be sorted to determine epithelial sequence 870. Epithelial sequence 870 comprises pulses sorted such that the laser beam expands from small 1 mm diameter to larger 4 mm diameter four times during the ablation.

Figure 8D:
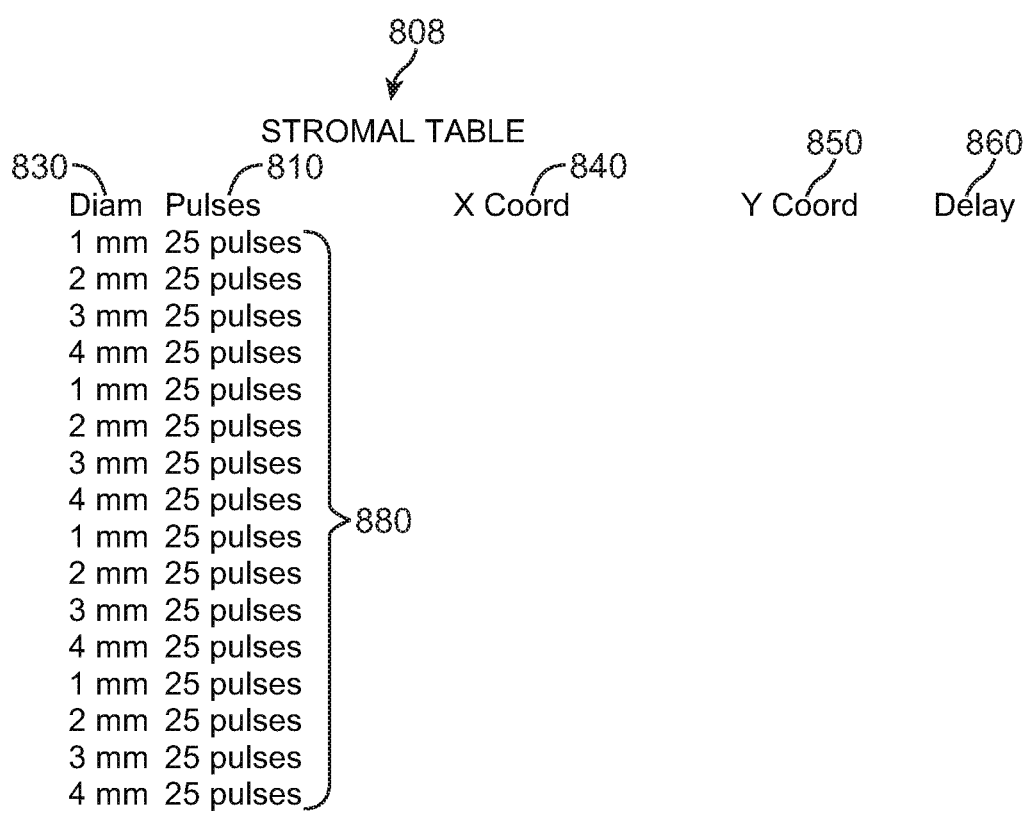
FIG. 8D is a simplified schematic illustration of a stromal treatment table that comprises stromal arrangement, according to embodiments of the present invention.

FIG. 8D is a simplified schematic illustration of a stromal treatment table 808 that comprises stromal arrangement 804, according to embodiments of the present invention. Stromal treatment table 808 comprises a stromal sequence 880 of laser beam pulses, which is determined based on the optical properties of the eye and/or healing as described above. Stromal arrangement 804 can be sorted to determine stromal sequence 880. Stromal sequence 880 comprises pulses sorted such that the laser beam expands from small 1 mm diameter to larger 4 mm diameter four times during the ablation.

Figure 8E:
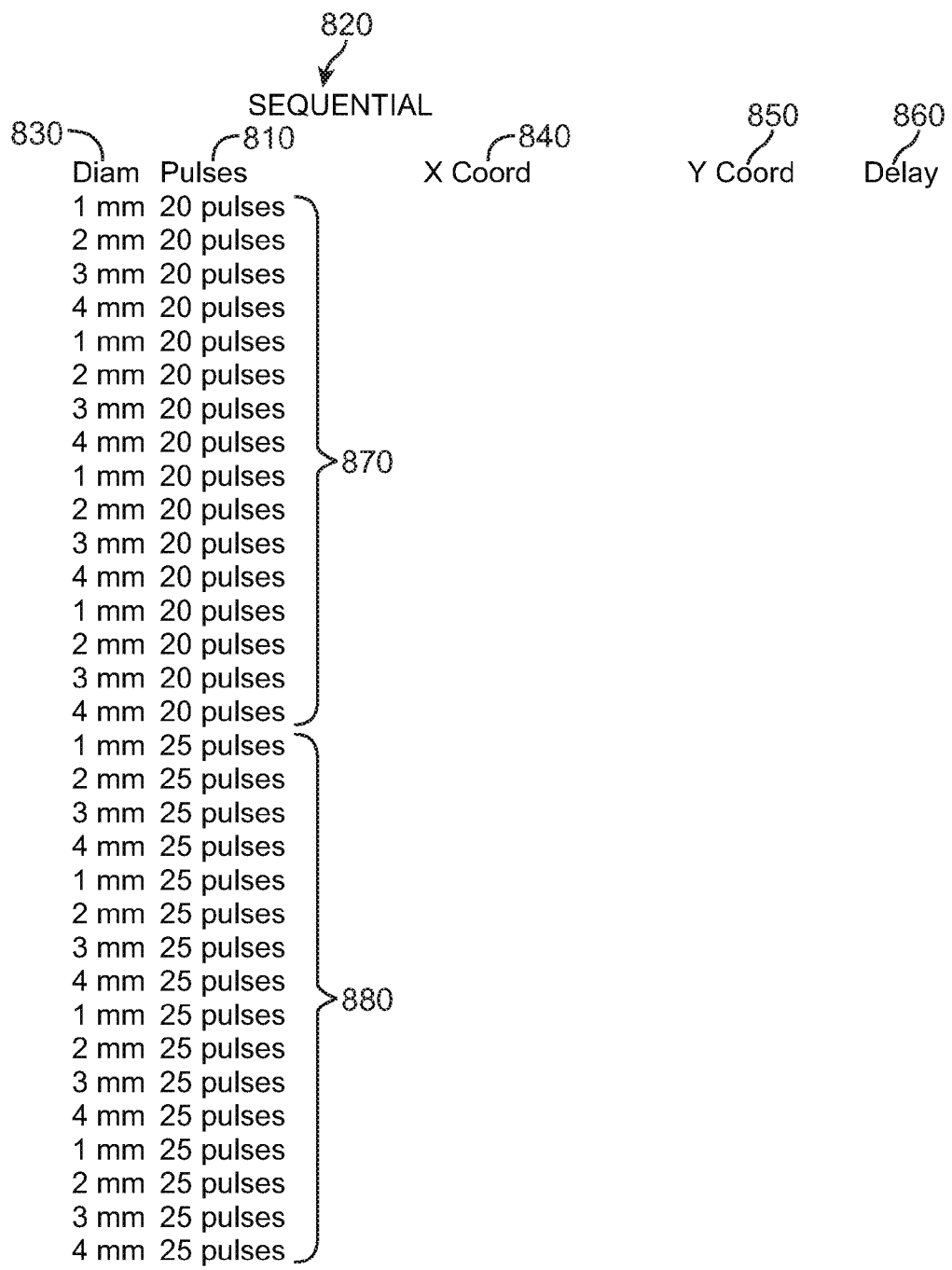
FIG. 8E is a simplified schematic illustration of a sequential treatment table that comprises epithelial sequence combined stromal sequence, according to embodiments of the present invention.

FIG. 8E is a simplified schematic illustration of a sequential treatment table 820 that comprises epithelial sequence 870 combined with stromal sequence 880, according to embodiments of the present invention. Epithelial sequence 870 is located before stromal sequence 880 such that epithelial sequence 870 ablates the epithelial layer in response to the mapped epithelial profile as described above. Pulse sequence 870 can remove the epithelial layer to expose the stromal layer and/or Bowman's membrane. Subsequent to removal of the epithelial layer, the stromal layer is ablated to a target ablation profile as described above. In some embodiments, the operator is able to interrupt the treatment upon penetration of the epithelial layer based on visual, or other, feedback from corneal epithelial and/or stromal fluorescence. In some embodiments, delay 860 is increased, for example from 50 ms to 200 ms, upon transition from epithelial sequence 870 to stromal sequence 880 to permit the operator to pause the treatment and mechanically remove the epithelial layer.

Figure 8F:
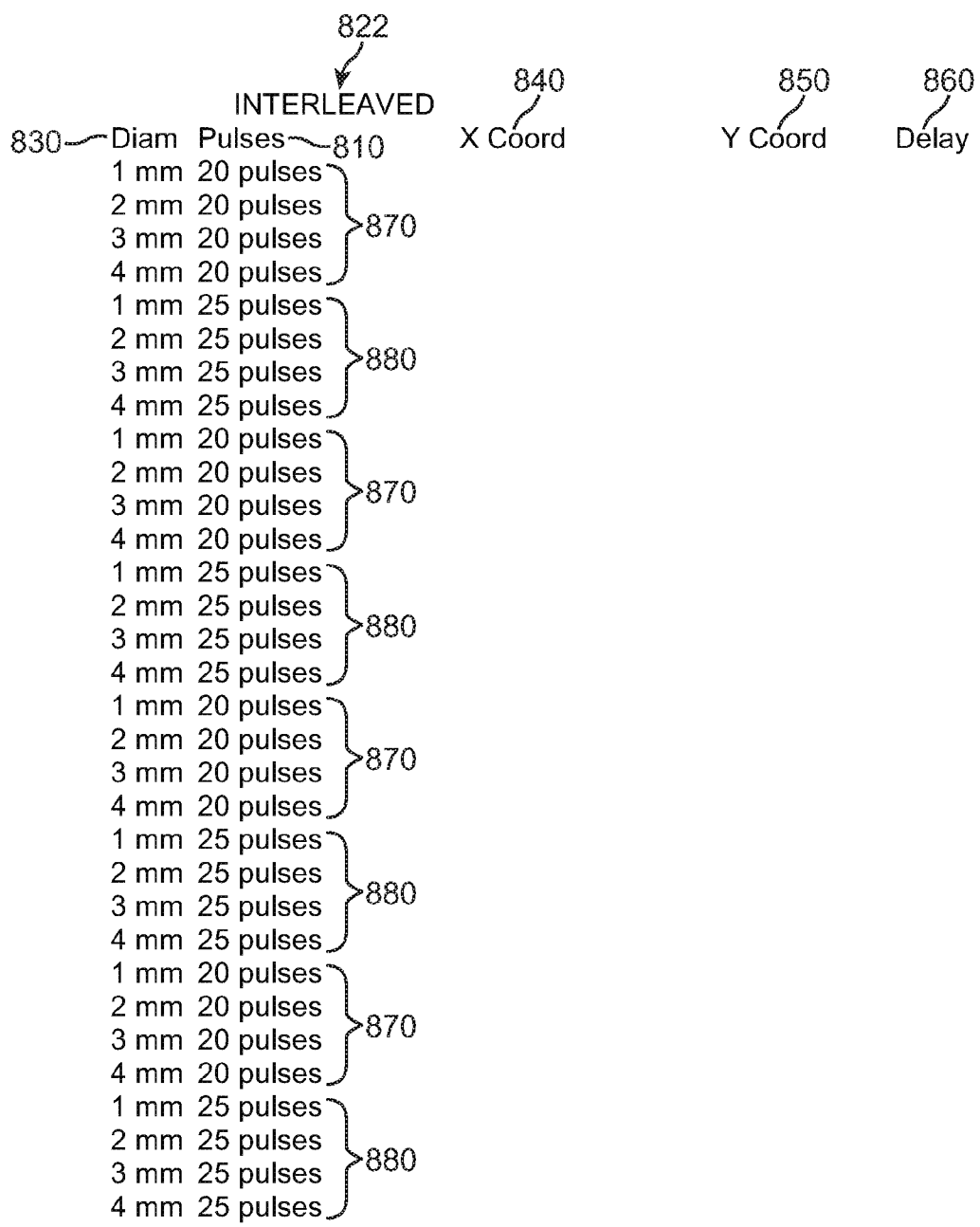
FIG. 8F is a simplified schematic illustration of an interleaved treatment table that comprises epithelial sequence interleaved with stromal sequence, according to embodiments of the present invention.

FIG. 8F is a simplified schematic illustration of an interleaved treatment table 822 that comprises epithelial sequence 870 interleaved with stromal sequence 880, according to embodiments of the present invention. Epithelial sequence 870 is interleaved with stromal sequence 880. Many pulses from stromal sequence 880 are placed at intervals among pulses from epithelial sequence 870 such that pulses from stromal sequence 880 are interspersed among pulses from epithelial sequence 870. Many of the pulses from stromal sequence 880 that are interspersed among epithelial pulses 870 are located near the beginning portion of the table such that pulses from stromal sequence 880 ablate the epithelial layer. Many pulses from epithelial sequence 870 are placed at intervals among pulses from stromal sequence 880 and located near the end portion of the table, such that pulses from epithelial sequence 870 are interspersed among stromal pulses so as ablate the stromal layer. The laser beam expands from small 2 mm diameter to larger 4 mm diameter eight times during the treatment.

One will appreciate that the embodiments shown in FIGS. 8A to 8F are merely examples of patterns, sequences, sorting techniques and treatment tables. Additional embodiments will be readily apparent to one or ordinary skill who will recognize variations, alternatives and modifications. For example, wide area pulses may be used to remove most of the epithelium followed by smaller pulses to remove epithelial and stromal tissue, and that some pulses may remove both epithelial and stromal tissue.

In some embodiments, an arrangement of pulses can be determined for Bowman's membrane, and Bowman's arrangement of pulses may be located within the treatment table in many ways. For example, the pulses that correspond to Bowman's membrane can be located in a treatment table at a location between epithelial pulses and stromal pulses. The epithelial pulses may be located near the beginning of the treatment table and stromal pulses located near the end of the treatment such that the location of the pulses in the treatment table corresponds to the tissue actually ablated with each pulse. In some embodiments, the treatment table may be interleaved such that Bowman's pulses are interspersed among epithelial and stromal pulses at many locations in the treatment table. The Bowman's pulses may be located near the beginning and near the end of the treatment table at locations in the treatment table that correspond to ablation of epithelial tissue and ablation of stromal tissue, respectively.

Figure 9:
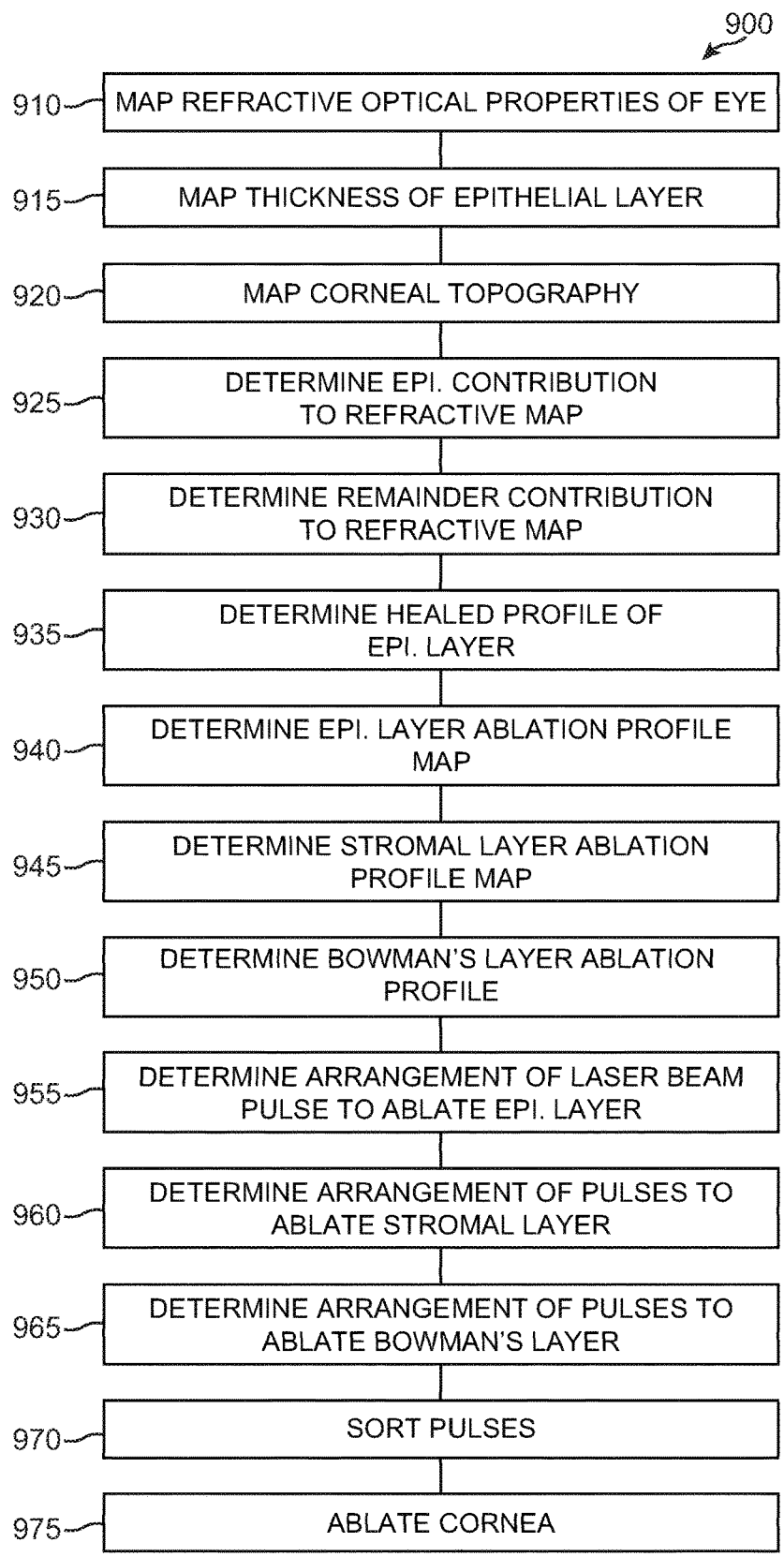
FIG. 9 is a flow chart that schematically illustrates a method of ablating the eye, according to embodiments of the present invention.

FIG. 9 is a flow chart that schematically illustrates a method 900 of ablating the eye, according to embodiments of the present invention. Method 900 includes a step 910 to map refractive optical properties of the eye. The refractive optical properties of the eye can be mapped in many ways; for example, with a wavefront system that measures the optical properties of the entire path of the eye. A step 915 maps thickness of the epithelial layer. The thickness of the epithelial layer can be mapped in many ways; for example, with an ultrasound machine. A step 920 maps corneal topography of the eye. The corneal topography of the eye of the eye can be mapped in many ways, as described above. A step 925 determines epithelial contribution to the refractive error map of the eye. The epithelial contribution of the refractive map of the eye can be determined from the thickness of the epithelial layer. A step 930 determines the remainder of contribution to the refractive map. The remainder of contribution can be determined by subtracting the epithelial contribution from the map of optical properties of the eye. A step 935 determines the healed profile of the epithelial layer. The healed profile of the epithelial layer can be determined in response to the ablation profile and/or a desired optical correction of the eye to correct optical properties of the eye. A step 945 determines stromal layer ablation profile map. The stromal layer ablation profile map can be determined from the healed profile of the epithelial layer and the remainder of contribution to the refractive map. A step 950 determines a Bowman's layer ablation profile. A step 955 determines an arrangement of laser beam pulses to ablate the epithelial layer. Step 955 uses epithelial basis data as described above. A step 960 determines an arrangement of laser pulses to ablate the stromal layer. Step 960 uses stromal basis data as described above. A step 965 determines an arrangement of pulses to ablate Bowman's layer to the profile determined in step 950. Step 965 uses Bowman's basis data as described above. A step 970 sorts the laser beam pulses. The pulses can be sorted in many ways, for example based on diameter of the pulse so that several small pulses are ablated before several large pulses, and several large pulses are ablated before several small pulses several times during the treatment. A step 975 ablates the cornea. The cornea is ablated with the stromal arrangement of the laser beam pulses and the epithelial arrangement of laser beam pulses, as described above.

It should be appreciated that the specific steps illustrated in FIG. 9 provide a particular method of ablating the eye, according to an embodiment of the present invention. Other sequences of steps may also be performed according to alternative embodiments. For example, alternative embodiments of the present invention may perform the steps outlined above in a different order. Moreover, the individual steps illustrated in FIG. 9 may include multiple sub-steps that may be performed in various sequences as appropriate to the individual step. Furthermore, additional steps may be added or removed depending on the particular applications. One of ordinary skill in the art would recognize many variations, modifications, and alternatives.

Embodiments of the present invention may use epithelial mapping without refractive correction to the stromal layer. For example, in some embodiments, the epithelium may be mapped as described above and epithelial and stromal treatments calculated to ablate haze or other optical irregularities from the cornea. In some embodiments, the epithelium may be ablated without stromal ablation to remove pathologies from the epithelium.

FIGS. 10A to 10H show examples of images of epithelial fluorescence from a patient treatment. The images shown in FIGS. 10A to 10H can be sampled from a treatment, for example a treatment of 1600 pulses. To obtain the images, a UV sensitive CCD camera can be mounted on the side of the microscope beam splitter and used to image the fluorescing event of each pulse, as described above. The camera may have its own frame-capture card located in the system controller computer. A "fire laser" signal, for example TTL (5 volt) signal, can be sent to the camera to trigger frame capture with each pulse, as described above. The exposure of the image may be timed such that the entire fluorescing event will be captured. The exposure time may be limited to 100 µs to avoid capturing unwanted light, including reflections from the patient illumination and room lighting.

Figures 10A, 10B, 10C, 10D:
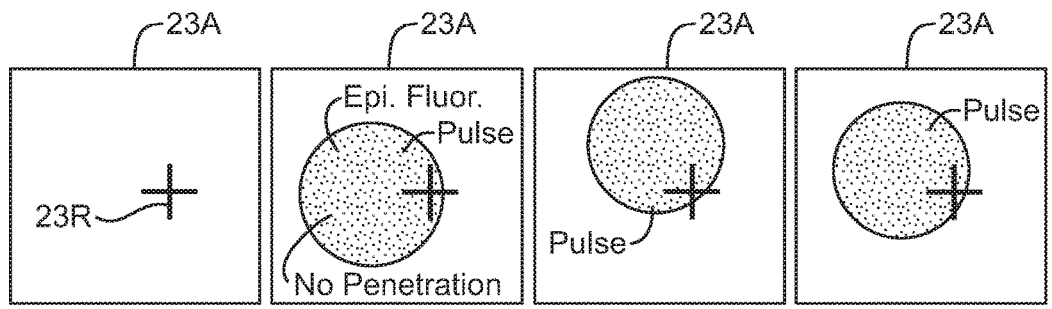
FIGS. 10A to 10H show examples of images of epithelial fluorescence, according to embodiments of the present invention.
Figures 10E, 10F, 10G, 10H:
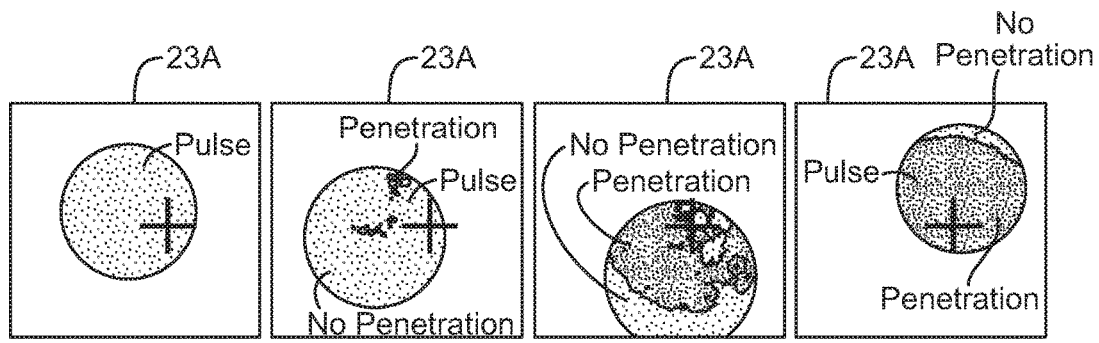

FIG. 10A shows a baseline image acquired when the laser is not fired and there is no epithelial fluorescence. FIG. 10B shows epithelial fluorescence with a first pulse at a first location, in which fluorescence extends across the first pulse location with an intensity above a threshold value. FIG. 10C shows epithelial fluorescence with a second pulse at a second location, in which fluorescence extends across the second pulse location with an intensity above the threshold value. FIG. 10D shows epithelial fluorescence with a third pulse at a third location, in which fluorescence extends across the third pulse location with an intensity above the threshold value. FIG. 10E shows epithelial fluorescence with a fourth pulse at a fourth location, in which fluorescence extends across the fourth pulse location with an intensity above the threshold value. FIG. 10F shows epithelial fluorescence with a fifth pulse at a fifth location, in which fluorescence extends across a majority of the area of the fifth pulse location with an intensity above the threshold value, and portions of the fifth pulse location comprise fluorescence intensity below the threshold value so as to indicate penetration of the epithelium. FIG. 10G shows epithelial fluorescence with a sixth pulse at a sixth location, in which fluorescence extends across a minority of the area of the sixth pulse location with an intensity above the threshold value, and portions of the sixth pulse location comprise fluorescence intensity below the threshold value so as to indicate penetration of the epithelium. FIG. 10H shows epithelial fluorescence with a seventh pulse at a seventh location, in which fluorescence extends across a minority of the area of the seventh pulse location with an intensity above the threshold value, and portions of the seventh pulse location comprise fluorescence intensity below the threshold value so as to indicate penetration of the epithelium.

The images shown in 10A to 10H comprise images sampled from a portion of the treatment, and similar images can be acquired from each pulse of the laser treatment for the entire treatment, for example with the camera triggered off the laser and coupled to the frame grabber and shown on the display as described above. The image from each pulse can be shown on the display in real time, such operator is able to visualize penetration of the epithelium with minimal interference from visible light, for example as shown in FIG. 10A which shows little interference from visible light at baseline.

Plotting General Intensity of Epithelial Fluorescence

Figure 11A:
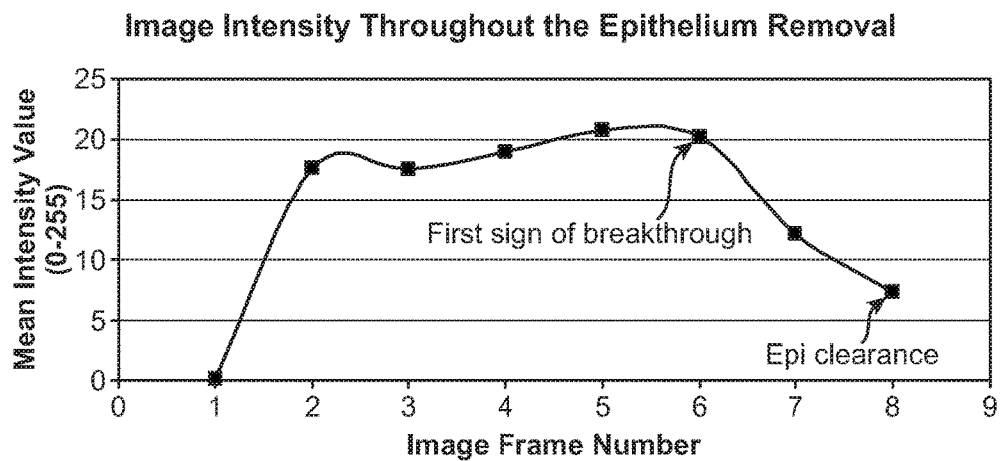
FIG. 11A shows a plot of image intensity for epithelium removal with images as in FIGS. 10A to 10H.

FIG. 11A shows a plot of image intensity for epithelium removal with images as in FIGS. 10A to 10H. This plot illustrates characteristics of the fluorescence images obtained with the above described system that can be used to detect penetration and/or clearance of the epithelium. Penetration/breakthrough of the epithelium can encompass at least some portion of the treatment area over which the epithelium which has been completely removed. Clearance of the epithelium may encompass removal of the epithelium over a majority of the surface area of the area targeted for removal. In many embodiments, penetration/breakthrough corresponds to a first amount of fluorescence and epithelial clearance corresponds to a second amount of fluorescence, the second amount smaller than the first amount.

The mean intensity value of a 20 pulse rolling average can be graphed to show intensity drop with penetration and/or epi clearance. Each laser beam pulse applied to the epithelium will fluoresce a certain threshold amount. Although the stroma may fluoresce, this amount can be substantially below the threshold amount. The amount of epithelial fluorescence can be quantified by summing the brightness value of each image for an empirical number of patients, for example 20 patients. As each pulse is applied, a specific image intensity can be expected because the exact area of epithelium irradiated is known based on the programmed size of the laser beam. By plotting the fluorescence values for each pulse, for example expected fluorescence minus measured, on a simple line graph inflexion points can signify breakthrough/penetration and clearance areas where epithelium has been removed. A running average of fluorescence values for a plurality of pulses may be used to determine penetration and/or clearance of the epithelium, for example a running average of 20 pulses. Therefore, a signal indicated epithelial penetration and/or clearance can be generated in response to at least one the laser beam size, a mean expected fluorescence value or running average of fluorescence. The signal may comprise a first signal to indicate penetration of the epithelium and a second signal to indicate clearance of the epithelium.

It is understood that other embodiments may fall within the spirit and scope of the invention. The scope of the invention should, therefore, be determined with reference to the appended claims along with their full scope of equivalents.

What is claimed is:

1. A method for treating a region of a cornea of an eye, the region comprising an epithelial layer disposed over a stromal layer, the method comprising:
    mapping a thickness of the epithelial layer in the region of the cornea to obtain a map profile of the epithelial layer;
    obtaining a wavefront map profile from measurements of refractive optical properties of the eye;
    calculating an optical path length for the map profile of the epithelial layer;
    deriving a remainder portion by subtracting the optical path length from the wavefront map profile;
    deriving a stromal ablation profile from the wavefront map profile, the stromal ablation profile including a remainder portion profile that corrects a wavefront error of the remainder portion;
    ablating the epithelial layer of the region of the cornea to expose the stromal layer according to the map profile of the epithelial layer; and
    ablating the stromal layer of the region of the cornea according to the stromal ablation profile.

2. The method of claim 1, wherein the refractive optical properties are mapped at locations distributed in two dimensions across a pupil of the eye and wherein the thickness of the epithelial layer is mapped at locations distributed in two dimensions.

3. The method of claim 1, wherein the map profile of the epithelial layer is registered with an iris of the eye.

4. The method of claim 1, further comprising determining an arrangement of laser beam pulses using the map profile of the epithelial layer, and wherein irradiation of the region is initiated using the determined arrangement.

5. The method of claim 1 further comprising interrupting the ablating of the epithelial layer of the region according to a tissue fluorescence of at least one of the epithelial layer or the stromal layer.

6. The method of claim 1 wherein energy is transmitted through the epithelial layer and/or reflected from an interface between the epithelial layer and the stromal layer while the region is mapped and wherein the energy reflected from the interface comprises at least one of optical energy or ultrasound energy.

7. The method of claim 1 wherein the optical properties comprises at least one of a manifest refraction, a cycloplegic refraction, an auto-refraction, a Zernike coefficient, a Fourier coefficient or a wavefront elevation map.

8. The method of claim 1 wherein the stromal layer is ablated according to a healed epithelial layer component.

9. The method of claim 1 further comprising determining a healed profile of the stromal layer and wherein the stromal ablation profile is additionally determined according to the healed stromal layer profile and a healed epithelial layer profile.

10. The method of claim 1, wherein the stromal ablation profile derived excludes a contribution of the optical path length of the epithelial layer.

* * * * *